US010774137B2

(12) United States Patent
Wooster et al.

(10) Patent No.: US 10,774,137 B2
(45) Date of Patent: Sep. 15, 2020

(54) COMPOSITIONS AND METHODS FOR REDUCING AT LEAST ONE SYMPTOM OF HUMAN ALLERGY TO CATS

(71) Applicant: Societe des Produits Nestle SA, Vevey (CH)

(72) Inventors: Timothy James Wooster, Epalinges (CH); Ebenezer Satyaraj, Wildwood, MO (US); Eddy Gombas, Lausanne (CH); Beat Gerber, Lausanne (CH)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 228 days.

(21) Appl. No.: 15/874,102

(22) Filed: Jan. 18, 2018

(65) Prior Publication Data
US 2019/0023772 A1    Jan. 24, 2019

Related U.S. Application Data

(60) Provisional application No. 62/449,883, filed on Jan. 24, 2017.

(51) Int. Cl.
C07K 16/18 (2006.01)
A61K 47/42 (2017.01)
A61K 9/00 (2006.01)
A61K 39/395 (2006.01)
A61K 47/36 (2006.01)
A61K 39/00 (2006.01)

(52) U.S. Cl.
CPC .............. C07K 16/18 (2013.01); A61K 9/006 (2013.01); A61K 39/395 (2013.01); A61K 47/36 (2013.01); A61K 47/42 (2013.01); A23V 2002/00 (2013.01); A61K 2039/505 (2013.01); C07K 2317/92 (2013.01)

(58) Field of Classification Search
None
See application file for complete search history.

(56) References Cited

U.S. PATENT DOCUMENTS 8,877,705 B2    11/2014  Larreta-Garde et al.
2013/0236475 A1  9/2013  Wells et al.

FOREIGN PATENT DOCUMENTS

| CN | 103251971 A | 8/2013 |
|---|---|---|
| CN | 104147627 A | 11/2014 |
| JP | 62289530 A | 12/1987 |
| WO | 9403159 | 2/1994 |
| WO | WO 2002/072636 * | 9/2002 ............... A61K 9/16 |
| WO | 2008103046 A1 | 8/2008 |
| WO | 2009009061 A1 | 1/2009 |
| WO | 2011048388 A2 | 4/2011 |

OTHER PUBLICATIONS

Yegappan et al. 'Carrageenan based hydrogels for drug delivery, tissue engineering and wound healing.' Carbohydrate Polymers vol. 198, Oct. 15, 2018, pp. 385-400.*
Muller et al., "IgY antibodies in human nutrition for disease prevention", Nutrition Journal, BioMed Central, vol. 14, Oct. 20, 2015, pp. 1-7, XP021230354.
International Search Report, Transmittal & Written Opinion, PCT/IB2018/050320.
Australian Microbiological Limits for Food, Issue 53 and 70, Standard 1.6.1.
Moritaka, et al., "Rheological Properties of Aqueous Agarose-Gelatin Gels", Journal of Texture Sudies 11 (1980) 257-270 Japan.
Fujii, et al. "Mechanical Properties of Two-Phase Disperse Agar/Gelatin Mixed Gels", Journal of Texture Studies 31 (2000) 273-286 Japan.
Bonferoni et al., Carrageenan-gelatin mucoadhesive systems for ion-exchange based opthalmic delivery: in vitro and preliminary in vivo studies European Journal of Pharmaceutics and Biopharmaceutics 57 (2004) 465-472 Italy.
Fang et al., "Associative and Segregative Phase Separations of Gelatin/k-Carrageenan Aqueous Mixtures", Langmuir 2006 22, 9532-9537 The Netherlands.
Jonganurakkun, et al., "Survival of lactic acid bacteria in simulated gastrointestinal juice protected by a DNA-based complex gel" J Biomater Sci Polymer Edn (2003) vol. 14 No. 11, pp. 1269-1281.
Coste, et al., "Study of the Poly-Lysine Release from Polysaccharides/Gelatin Hydorgels", Proceed. Int'l Symp. Control. Rel. bioact. Mater, 27(2000) Controlled Release Society, pp. 744-745 France.
Lam, et al., "Development of formaldehyde-free agar/gelatin microcapsules containing berberine HCl and gallic acid and their topical and oral applications", Soft Matter 2012, 8 5027-5037.
Girod, et al. "Characerization of a gelatin/polysaccharides mixed hydrogel," Proceeds Int'l. Symp. Control. Rel. Boact. Mater 2000 27th 760-761.
Devi, et al., Genipin crosslinked microcapsules of gelatin A and k-carrageenan polyelectrolyte complex for encapsulation of Neem (Azadiracta Indica A.Juss) seed oil Polym.Bull. 2010 65 374-362.
Varghese, et al. "Gelatin-carrageenan hydrogels: Role of pore size distribution on drug delivery process" Colloids and Surfaces B. Biointerfaces 2014 113, 346-351 India.

(Continued)

Primary Examiner — Nora M Rooney

(57) ABSTRACT

Compositions and methods reduce symptoms of human allergy to cats. The effectiveness of a molecule which specifically binds to *Feline domesticus* allergen number 1 (Fel D1) is enhanced by prolonging the time the immunoglobulin stays within the mouth of a cat to whom the anti-Fel D1 molecule is administered in a pet food. The compositions and methods use a powder that is a dried hydrogel encapsulating the anti-Fel D1 molecule, and the hydrogel is based on gelatin, collagen peptides, or gelatin and collagen peptides; and carrageenan. The methods of making the powder provide a high encapsulation efficacy, sustained release of the anti-Fel D1 molecule in the cat's mouth, and oral adhesion of the anti-Fel D1 molecule in the cat's mouth.

9 Claims, 24 Drawing Sheets

(56) References Cited

OTHER PUBLICATIONS

Saxena, et al. "Rheological properties of binary and ternary protein-polysaccharide co-hydrogels and comparative release kinetics of salbutamol sulphate from their matrices" International Journal of Biological Macromolecules 2011 48, 263-270 India.

Devi et al., Microencapsulation of isoniazid in genipin-crosslinked gelatin-A-k-carrageenan polyelectrolyte complex Drug Development and Industrial Pharmacy 2010 36(1) 56-63 India.

Lundin, et al., "Phase Separation in Mixed Carrageenan Systems", Proceedings to Supermolecular and Colloidal Structures in Biomaterials and Biosubstrates 1999 (Supplied by the British Library) pp. 436-449.

https://www.youtube.com/watch?v=6bYlow9pc6M Published on Feb. 21, 2011 Connect with GELITA: Visit our Website: https://www.gelita.com/.

* cited by examiner

FIG. 17

| Sample Name | Gelatin 280 Bloom | Gelatin 100 Bloom | Kappa Carrageenan (WR78) | Whey Protein | Powder Quality | Mean g/cm3 | Stdev | inlet (°C) | outlet (°C) | humid (%) | nozzle pressure |
|---|---|---|---|---|---|---|---|---|---|---|---|
| *i) comparison gelatin molecular weight* | | | | | | *0.1 to 0.15* | | | | | |
| TJW 020A | 10 | 0 | 0 | 2 | | | | | | | |
| TJW 106 | 0 | 10 | 0 | 10 | | 0.265 | 0.005 | 160 | 80 | 2400% | 2bar |
| *ii) comparison active ingredient/excipient conc. (WPI)* | | | | | | | | | | | |
| TJW 040A | 0 | 10 | 0 | 2.5 | | 0.190 | 0.004 | 160 | 78.3 | 24 | 2 bar |
| TJW 040B | 0 | 10 | 0 | 2.5 | | 0.209 | 0.005 | 120 | 61 | 32 | 1 bar |
| TJW 040C | 0 | 16 | 0 | 4 | | 0.098 | 0.003 | 120 | 60 | 24 | 1 bar |
| TJW 040D | 0 | 10 | 0 | 10 | | 0.236 | 0.004 | 120 | 63 | 25 | 1 bar |
| TJW 045C | 0 | 10 | 1.5 | 7.7 | | 0.141 | 0.005 | 140 | 58 | 27 | 2 bar |
| *iii) comparison active ingredient/excipient conc. (egg yolk)* | | | | | | | | | | | |
| TJW 050A | 0 | 10 | 0 | 5 | | 0.294 | 0.010 | 160 | 74 | 18 | 1 bar |
| TJW 106 | 0 | 10 | 0 | 10 | | 0.265 | 0.005 | 160 | 80 | 24 | 2bar |
| *iv) reference dairy powder* | | | | | | | | | | | |
| WPI 95 | | | | | | 0.428 | 0.004 | | | | |

FIG. 19

Table 1: compositions of test samples

| Test sample | 1 (control) | 2 |
|---|---|---|
| Egg yolk protein | 94 wt% | 47wt% |
| Porcine Gelatine (Type A, 100 bloom) | - | 47wt% |
| salt | - | 0.1 wt% |
| Moisture | 6 wt% | 6 wt% |
| Administered Dose | 1 gram | 2.5 grams |
| IgY Dose | 140 mg | 140 mg |

COMPOSITIONS AND METHODS FOR REDUCING AT LEAST ONE SYMPTOM OF HUMAN ALLERGY TO CATS

CROSS REFERENCE TO RELATED APPLICATIONS

This application claims priority to U.S. Provisional Application No. 62/449,883 filed Jan. 24, 2017, the disclosure of which is incorporated herein by this reference.

BACKGROUND

Approximately 20% of adults suffer from allergy to cats and/or their dander. Symptoms of cat allergies range from mild rhinitis and conjunctivitis to life-threatening asthmatic responses, and cat allergies are a major roadblock to cat ownership. For example, cat allergy is the primary reason given by cat owners for returning cats to animal shelters.

Most cat allergies are caused by a small stable glycoprotein called Fel D1 (*Feline domesticus* allergen number 1). This protein is transferred to cat dander by their grooming process and becomes airborne. Upon inhalation of cat dander having Fel D1 attached, an allergy cascade is triggered because of the recognition of the Fel D1 by human immune cells.

SUMMARY

The present disclosure is directed to oral adhesion/mucoadhesion of a molecule which specifically binds to Fel D1, hydrogel technology for controlled release of the anti-Fel D1 molecule, and processing approaches to create a powder from the hydrogel. This anti-Fel D1 molecule (e.g., an egg immunoglobulin such as IgY from an avian immunized with Fel D1) can reduce at least one symptom of human allergy to cats because it blocks the recognition of the Fel D1 by the human immune cells. The proposed site of action of this anti-Fel D1 molecule is within the cat's mouth where the Fel D1 protein is secreted and/or on the cat's fur where the Fel D1 is deposited during the grooming process.

The present inventors propose delivery of the anti-Fel D1 molecule to cats via their food. The initial animal trials indicated that administration of this molecule to cats via their food only results in an approximately 30-35% reduction in free Fel D1 in cat saliva. The present inventors believe that the main limitation is the need for the anti-Fel D1 molecule to stay in the cat's mouth for a long period of time, but the process of eating and drinking results in a large amount of the molecule administered in food being swallowed and thus not having an effect. Increasing IgY oral residence can be measured in two distinct ways. In one aspect, the IgY can be measured as having a higher concentration at a specific point in time, e.g., after 5 minutes of eating. In another aspect, the IgY can be measured as taking longer to decrease below a certain threshold, e.g, more than 10 ug/ml, ≥1 ug/ml or even >100 ng/ml.

The present inventors believe that one of the primary challenges in creating a controlled-release hydrogel for delivery in a cat's mouth is to ensure that the hydrogel dissolve instantaneously, not melt, within the cat's mouth, has mucoadhesive properties, and is appealing to cats. Chitosan is a well-known highly mucoadhesive polymer but is mucoadhesive at acidic pHs, and cats' mouths and typical pet foods have neutral pHs. Another leading mucoadhesive polymer is porcine gelatin, but gels created from gelatin melt at body temperatures.

As detailed in the experimental results disclosed later herein, the present inventors surprisingly found that an additional biopolymer can control the melting/dissolution of a gelatin-based hydrogel. Specifically, wet hydrogels that were gelatin/kappa-carrageenan co-gels provided slower release of an anti-Fel D1 immunoglobulin (IgY). This finding was unexpected because combinations of biopolymers do not typically lead to good gels because the two polymers undergo phase separation. Lundin, L. O., Odic, K. and Foster, T. J. (1999) Phase separation in mixed carrageenan systems. *Proceedings to Supermolecular and Colloidal Structures in Biomaterials and Biosubstrates*, Mysore, India.

Accordingly, in one embodiment, a food grade powder providing sustained release of an anti-Fel D1 molecule is provided. The food grade powder can comprise a dried hydrogel and the anti-Fel D1 molecule; wherein the dried hydrogel comprises gelatin, collagen peptides, or gelatin and collagen peptides; and carrageenan; wherein the anti-Fel D1 molecule is encapsulated in the dried hydrogel.

Additionally, in an embodiment, the present disclosure provides a method of making a food grade powder providing sustained release of an anti-Fel D1 molecule. The method comprises: heating a solution comprising gelatin, carrageenan and the anti-Fel D1 molecule; forming droplets of the heated solution; gelling the droplets by subjecting the droplets to a gelling bath comprising salt or oil to form gelled beads in which the anti-Fel D1 molecule is encapsulated; and drying the gelled beads to form the food grade powder.

The droplets can be formed by passing the heated solution through a nozzle. The heating of the solution can comprise subjecting the solution to a temperature of about 60° C. The gelling bath can comprise about 100 mM of potassium chloride. The drying can comprise subjecting the beads to fluid bed drying.

The present inventors also noted that the most common approach to drying in the food industry is spray drying but found that conventional spray drying of gelatin or gelatin/carrageenan compositions lead to rapid release of an anti-Fel D1 molecule (IgY) during in vitro testing due to a highly porous powder structure. Surprisingly, the present inventors found that when the compositions were gelled before drying, release of the anti-Fel D1 molecule during in vitro testing was considerably slower. For example, an extrusion process led to a higher percentage of encapsulation and a greater ability to control the final size of the powder particle. Interestingly, the extrusion process resulted in a much better structure (smoother surface, fewer inclusions) when carrageenan was incorporated into the mixture prior to extrusion.

Accordingly, in an embodiment, the present disclosure provides a method of making a food grade powder providing sustained release of an anti-Fel D1 molecule. The method comprises: heating a solution comprising gelatin, carrageenan, and the anti-Fel D1 molecule; extruding the heated solution to cool the heated solution and form an extruded hydrogel in which the anti-Fel D1 molecule is encapsulated; and drying the extruded hydrogel.

The method can comprise milling the dried hydrogel to a predetermined size. The heating of the solution can comprise subjecting the solution to a temperature of at least about 60° C. before the extruding and can further comprise subjecting the solution to a holding tank having a temperature of at least about 40° C. and then transferring the solution from the holding tank to another device which subjects the solution to the temperature of at least about 60° C. The extruding can be performed by a tubular heat exchanger having a temperature of about 5° C. to about 55° C., or in one aspect, of about 5° C. to about 35° C., and at least a portion of the heating of the solution can be conducted in a funnel and/or a pump of the tubular heat exchanger. The method can comprise immersing the extruded hydrogel in a composition comprising calcium before the drying. The drying can comprise subjecting the extruded hydrogel to a drying tunnel, oven, or fluid bed drier.

In another embodiment, the present disclosure provides a food grade powder providing sustained release of an anti-Fel D1 molecule. The food grade powder comprises a dried hydrogel comprising gelatin, collagen, or gelatin and collagen peptides; carrageenan; and the anti-Fel D1 molecule; where the anti-Fel D1 molecule is encapsulated in the dried hydrogel. The powder can be made by one of the two methods noted above.

The present inventors also noted that it is well known that spray drying gelatin is very difficult. The reason is that gelatin solutions at high total solids have high elasticity which forms long filaments during the atomization of spray drying. The formation of filaments during the spray drying process results in a powder which has very low porosity and is very fluffy, and both of these features severely limit powder flowability and processing capabilities.

The present inventors surprisingly found that optimized spray drying conditions and also careful selection of gelatin properties (e.g., molecular weight) and wall materials could develop a formulation capable of being spray dried, with the resulting powder retaining its mucoadhesive properties. Notably, a powder which is created simply by dry mixing the gelatin and the anti-Fel D1 molecule will not result in increased oral retention of the anti-Fel D1 molecule because the anti-Fel D1 molecule is not encapsulated.

Accordingly, in an embodiment, the present disclosure provides a method of making a food grade powder providing sustained release of an anti-Fel D1 molecule. The method comprises spray drying a solution comprising an anti-Fel D1 molecule and 5.0 to 20.0 wt. % of gelatin having a bloom value of 40 to 300, in one aspect, 40 to 300, or even about 100, to form a dried hydrogel in which the anti-Fel D1 molecule is encapsulated.

The resultant powder can be a food grade powder providing sustained release of an anti-Fel D1 molecule and comprising a dried hydrogel comprising the anti-Fel D1 molecule and 0.5 to 90 wt. % of gelatin. The anti-Fel D1 molecule is encapsulated in the dried hydrogel, and the powder can have a density of about 0.265 to about 0.3 g/cm$^3$. In an embodiment, the gelatin can be Type A porcine gelatin having a positive charge at a pH below 7.0 and can be the only biopolymer capable of gelling below 60° C. in the dried hydrogel. In one embodiment, the gelatin and collagen peptides can have a molecular weight between 2,000 and 1 million Daltons and/or a bloom value of 40 to 300.

The present disclosure also provides a method of reducing symptoms of human allergy to a cat. The method comprises orally administering to the cat an effective amount of any of the embodiments of the food grade powder disclosed herein and/or a food grade powder resulting from any of the methods of making a food grade powder disclosed herein. The powder can be administered as part of a pet food further comprising at least one component selected from the group consisting of protein, fat, carbohydrate, vitamin and mineral.

An advantage of one or more embodiments provided by the present disclosure is to reduce, minimize or prevent at least one symptom of an allergic reaction to a cat in a sensitized human.

Another advantage of one or more embodiments provided by the present disclosure is to reduce, minimize, or prevent allergies caused by cats.

Another advantage of one or more embodiments provided by the present disclosure is to expose a cat's mouth to a molecule that binds FelD1 before it contacts a sensitive human; a bound allergen cannot interact with the mast cells in the human and thereby cannot cause an allergenic reaction.

A further advantage of one or more embodiments provided by the present disclosure is a carrier/delivery system that enhances the oral residence time of an anti-Fel D1 molecule in a cat's mouth and is highly appealing to the cat (e.g., administrable in a pet food).

A further advantage of one or more embodiments provided by the present disclosure is to increase owner appeal, increase cat ownership, and improve the health of adults and children in cat-owning households.

Still another advantage of one or more embodiments provided by the present disclosure is to use multiple technologies to reduce symptoms of human allergy to cats.

Yet another advantage of one or more embodiments provided by the present disclosure is to control the melting/dissolution of a hydrogel encapsulating the active molecule.

Another advantage of one or more embodiments provided by the present disclosure is to address cat allergy using a diet of the cat and thereby reduce or remove the need for the allergic human to take medication or avoid contact with the cat.

A further advantage of one or more embodiments provided by the present disclosure is to provide a powder having a high content of an anti-Fel D1 molecule due to high encapsulation efficacy (e.g., by using in situ gelation instead of gelation bath) and/or minimal loss of the anti-Fel D1 molecule (e.g., by coping with higher viscosity matrices associated with lower temperatures).

Still another advantage of one or more embodiments provided by the present disclosure is easy formation of extruded encapsulated materials due to gelation temperature profile, strand strength, and lubrication properties.

Additional features and advantages are described herein and will be apparent from the following Detailed Description and the Figures.

BRIEF DESCRIPTION OF THE FIGURES

FIGS. 5A-5D contain photographs showing the visual appearance of different hydrogels prepared from solutions of 10 wt. % gelatin type A and 2 wt. % egg yolk extract. Samples were prepared as: (FIG. 5A) gel piece 3×20×20 mm, (FIG. 5B) spray dried powder (Diameter, D4,3 32 μm), (FIG. 5C) wet beadlet produced by dripping into oil, and (FIG. 5D) dried beadlet produced from (III).

(FIG. 6A) by spray drying or (FIG. 6B) by dripping followed by fluidized bed drying.

(FIG. 7A) freeze fracture cryo-SEM, (FIG. 7B) cryo-SEM with ice sublimation, (FIG. 7C) cryo-SEM with extended ice sublimation and (FIG. 7D) SEM of dried beadlet.

FIG. 17 is a table showing the composition and powder properties (physical appearance and density) of different spray dried gelatin powders. Powder quality index: 1—can't pump liquid, 2—blocked nozzle, 3—extensive spider webs, 4—fluffy powder, 5—medium dense power, 6—dense powder.

FIG. 19 is a table showing the composition of the two test samples used in the human clinical trial used to assess the impact of encapsulation on IgY oral retention.

DETAILED DESCRIPTION

Definitions

Figure 1A:
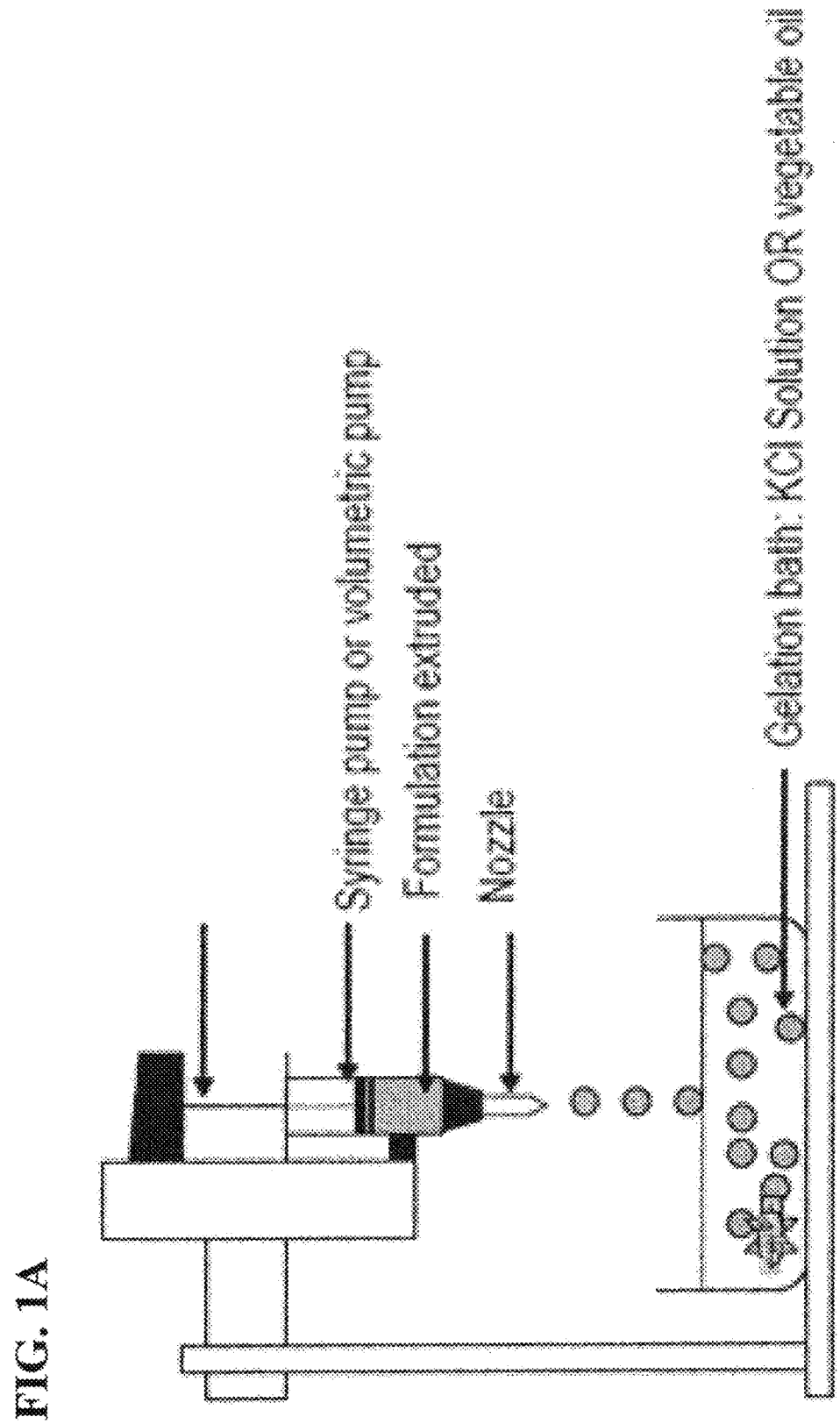
FIG. 1A is a schematic diagram of a system that can be used in an embodiment of a first method of making a food grade powder that reduces at least one symptom of human allergy to cats (the "dripping method").

As used in this disclosure and the appended claims, the singular forms "a," "an" and "the" include plural referents unless the context clearly dictates otherwise. The words "comprise," "comprises" and "comprising" are to be interpreted inclusively rather than exclusively. Likewise, the terms "include," "including" and "or" should all be construed to be inclusive, unless such a construction is clearly prohibited from the context. However, the devices disclosed herein may lack any element that is not specifically disclosed. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

Ranges are used herein in shorthand to avoid listing every value within the range. Any appropriate value within the range can be selected as the upper value or lower value of the range. Moreover, the numerical ranges herein include all integers, whole or fractions, within the range.

All percentages expressed herein are by weight of the total weight of the composition unless expressed otherwise. When reference is made to the pH, values correspond to pH measured at 25° C. with standard equipment. As used herein, "about" or "substantially" in reference to a number is understood to refer to numbers in a range of numerals, for example the range of −10% to +10%, −5% to +5%, −1% to +1%, or in one aspect, −0.1% to +0.1% of the referenced number.

"Food grade" means that the powder is edible by a cat and is not toxic to the cat. For example, a food grade powder contains a maximum of 5.0 wt. % of glycerol.

The term "allergy" is synonymous with "allergic response" or "allergic reaction." Each of the terms refers to a state of immune responsiveness in an animal specific to an exogenous antigen (or "allergen") that is not otherwise harmful to the animal. A "symptom" of an allergic response refers to any measure of the immune responsiveness, e.g., on the molecular level (including measurement of an activity or expression of a protein, or transcript or gene), the cellular level, the organ level, the systemic level, or the organism level. Such symptoms can comprise one or more such levels. "Reducing at least one symptom" includes reducing such symptoms before they occur so that there are no symptoms to an allergic response and thus preventing the allergic response.

Symptoms may include generalized phenomena such as inflammation, respiratory complaints, swelling, or distress typically associated with allergy, rhinitis, edema, and allergic skin disorders including but not limited to atopic dermatitis (e.g., eczema), urticaria (e.g., hives) and angioedema, and allergic contact dermatitis. More specific phenomena that are "symptoms" of an allergic response include any measurable or observable change, for example at the cellular level, including but not limited to local or systemic changes in cell populations, eosinophilia, recruitment and/or activation of immune cells, including, for example, mast cells and/or basophils, changes in antigen-presenting cells (including but not limited to FcεRI-bearing dendritic cells), intracellular or molecular changes, including measurement or observations of one or more steps in an immunological cascade, release of intracellular compounds that mediate an allergic response (e.g., mediators), and changes in one or more cytokines (e.g., IL-3, IL-5, IL-9, IL-4, or IL-13) or related compounds or antagonists thereof. The skilled artisan will understand that certain symptoms as defined herein are more readily measured than others, and some are measured through subjective assessment or self-assessment of the symptom. For other symptoms, there are convenient or rapid assays or measurements for objectively assessing changes.

As used herein, an "effective amount" is an amount of any the compositions disclosed herein administered to a cat that reduces at least one symptom of cat allergy in a sensitized human in the same environment as the cat (e.g., a house, room, car, office, hotel, yard, garage). The relative term "reducing at least one symptom" and similar terms refer to a reduced severity resulting from the compositions and methods disclosed herein relative to the severity if the compositions and methods are not used but conditions are otherwise identical. As used herein, "reducing at least one symptom" includes, but is not limited to, reducing such symptoms before they occur so that there are no symptoms to an allergic response and thus preventing the allergic response.

As used herein, an "anti-Fel D1 molecule" is any molecule able to specifically bind *Feline domesticus* allergen number 1 (Fel D1), for example an antibody, an aptamer, an agonist/antagonist of Fel D1, or portions of such molecules (e.g., an antigen binding fragment (Fab) of an antibody). The term "antibody" includes polyclonal and monoclonal antibodies of any type and from any species, as well as immunoglobulin fragments such as Fv, Fab, Fab', F(ab')$_2$, or other antigen-binding antibody fragments, sequences or subsequences that interact with molecular specificity (e.g., demonstrate specific binding) with an antigen.

In one embodiment, the anti-Fel D1 molecule is an antibody (e.g., IgY) produced by immunizing an avian such as a chicken with Fel D1 to cause production of the antibody in eggs. The antibodies can be separated from the egg and administered to the animal; or the eggs and/or a part of the eggs such as the egg yolk can be applied directly onto or admixed with a food or other composition suitable for administration to an animal. In one aspect, the anti-Fel D1 molecule can be one of the embodiments of the molecules disclosed in U.S. Pat. No. 8,454,953 to Wells et al., "Methods for reducing allergies caused by environmental allergens," incorporated herein by reference in its entirety.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, specific devices, methods, articles of manufacture, or other means or materials are described herein.

Embodiments

The present disclosure relates generally to compositions and methods of using an active molecule that reduces at least one symptom of human allergy to cats. More specifically, the present disclosure is directed to enhancing the effectiveness of the active molecule by prolonging the time the active molecule stays within the mouth of a cat administered the active molecule and/or increasing the concentration of active molecule detected in the mouth. Increasing the active molecule, e.g., IgY, oral residence can be measured in two distinct ways. In one aspect, the active molecule can be measured as having a higher concentration at a specific point in time, e.g., after 5 minutes of eating. In another aspect, the active molecule can be measured as taking longer to decrease below a certain threshold in the oral cavity, e.g., more than 10 ug/ml, ≥1 ug/ml, or even >100 ng/ml.

An aspect of the present disclosure is a food grade powder that provides sustained release of an anti-Fel D1 molecule. The anti-Fel D1 molecule is encapsulated in the dried hydrogel.

In an embodiment, the food grade powder comprises a dried hydrogel comprising gelatin, carrageenan and the anti-Fel D1 molecule. In one aspect, the gelatin and the carrageenan are the only biopolymers capable of gelling below 60° C. in the dried hydrogel. In another aspect, the gelatin and the carrageenan are the only non-allergy reducing biopolymers. The gelatin can be from any source, such as pig, beef, or fish. In one aspect, the gelatin used with the carrageenan is Type A gelatin (acid-treated), has a positive charge and has a moderate molecular weight between 2,000 and 2,000,000 Daltons (i.e. 40 to 300 bloom), or in one aspect between 100 to 200 bloom. For example, in one specific embodiment is porcine gelatin having a positive charge at pHs below 7.0.

The carrageenan can be any carrageenan from an algal or vegetable source (e.g., kappa, iota or gamma carrageenan). In one aspect, the carrageenan gels can include salt ions (e.g. potassium, calcium, magnesium, sodium). For example, the carrageenan can be kappa carrageenan, iota carrageenan, a co-polymer of kappa carrageenan and iota carrageenan or a mixture of kappa carrageenan and iota carrageenan. One aspect is a carrageenan that gels in the presence of potassium, i.e., kappa carrageenan or a co-polymer of kappa carrageenan and iota carrageenan.

The food grade powder can comprise a source of the anti-Fel D1 molecule. In one aspect, the anti-Fel D1 molecule can be anti-Fel D1 IgY, and a source can be partially defatted egg yolk powder from an avian immunized with Fel D1. The powder can comprise 0.5 to 90 wt. % of the gelatin, 0.1 to 50 wt. % of the carrageenan and 10 to 99.5 wt. % of the source of the anti-Fel D1 molecule; in one aspect, 10.0 to 80.0 wt. % of the gelatin, 0.5 to 20 wt. % of the carrageenan and 20 to 89.5 wt. % of the source of the anti-Fel D1 molecule; and in one specific aspect, 20.0 to 80.0 wt. % of the gelatin, 1 to 10 wt. % of the carrageenan and 19 to 79 wt. % of the a source of the anti-Fel D1 molecule; and in still another aspect, 25.0 to 60.0 wt. % of the gelatin, 1 to 10 wt. % of the carrageenan and 39 to 74 wt. % of the a source of the anti-Fel D1 molecule.

Figure 1B:
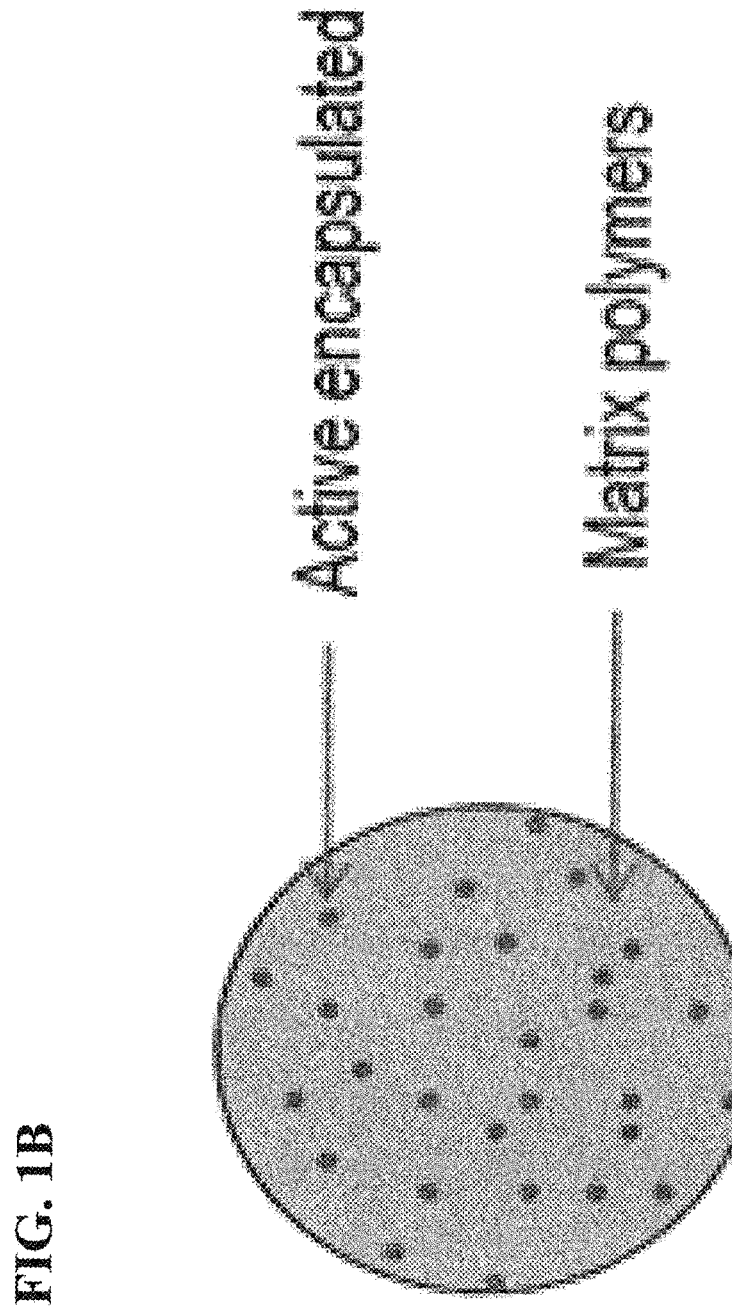
FIG. 1B is a schematic diagram of an embodiment of a food grade powder made by the dripping method.

Another aspect of the present disclosure is a method of making a food grade powder providing sustained release of an anti-Fel D1 molecule, for example the powder comprising gelatin, carrageenan and an anti-Fel D1 molecule as disclosed above. The method can comprise heating a solution comprising gelatin, carrageenan and the anti-Fel D1 molecule, in one aspect, to a temperature of about 60° C. The method can further comprise forming droplets of the heated solution, for example by passing the heated solution through a nozzle. The matrix material (the gelatin and the carrageenan) can be atomized by the nozzle. FIG. 1A is a schematic diagram of a non-limiting example of a suitable apparatus for performing this method, and FIG. 1B is an illustration of the active compound (the anti-Fel D1 molecule) encapsulated in the gelatin-carrageenan co-polymer formed by this method.

The droplets can be gelled by subjecting the droplets to a gelling bath comprising salt or oil, for example by dripping, jetting or prilling the droplets into the bath, to form gelled beads in which the anti-Fel D1 molecule is encapsulated. In an embodiment, a syringe pump or volumetric pump pushes the heated solution through the nozzle into the gelling bath.

The bath can comprise about 25-100 mM of potassium chloride or 100 mM calcium chloride, or both. In this regard, the present inventors found that some embodiments in which potassium chloride concentrations higher than 100 mM were used lead to carrageenan melting points which are too high and thereby increase processing temperatures and cause considerable loss (30-80%) of activity of the anti-Fel D1 molecule due to denaturation. In some embodiments, the potassium chloride can be partially or completely replaced by calcium chloride.

The gelled beads can be collected, optionally washed, and dried to form the food grade powder. In one aspect, the gelled beads can be dried by fluid bed drying. For example, the washed wet beads can be dried in a fluid bed drier with an inlet air temperature of 25° C. at an air flow of 80 m$^3$/minute for 3 to 5 hours.

Although the method detailed above is suitable for making a food grade powder providing sustained release of an anti-Fel D1 molecule, the present inventors discovered an extrusion process in which a higher percentage of the anti-Fel D1 molecule is encapsulated and there is a greater ability to control the final size of the powder particle. Furthermore, this extrusion process surprisingly resulted in much better structure (e.g., smoother surface, fewer inclusions) when carrageenan was incorporated into the mixture prior to extrusion.

Therefore, the present disclosure provides another embodiment of a method of making a food grade powder providing sustained release of an anti-Fel D1 molecule and comprising gelatin, carrageenan and the anti-Fel D1 molecule. The method can comprise heating a solution comprising gelatin, carrageenan, and the anti-Fel D1 molecule in a holding tank that has a temperature of at least about 40° C. Then the solution can be heated to a temperature of at least about 50-60° C., for example in a funnel and/or a pump of a tubular heat exchanger. Then the tubular heat exchanger can cool the heated solution and extrude a hydrogel in which the anti-Fel D1 molecule is encapsulated. For example, the tubular heat exchanger can have a temperature of about 15° C. to about 25° C. In one aspect, the method does not employ a gelation bath and thereby avoids the losses associated with such a bath, for example from washing and collecting the gelled beads.

Figure 2A:
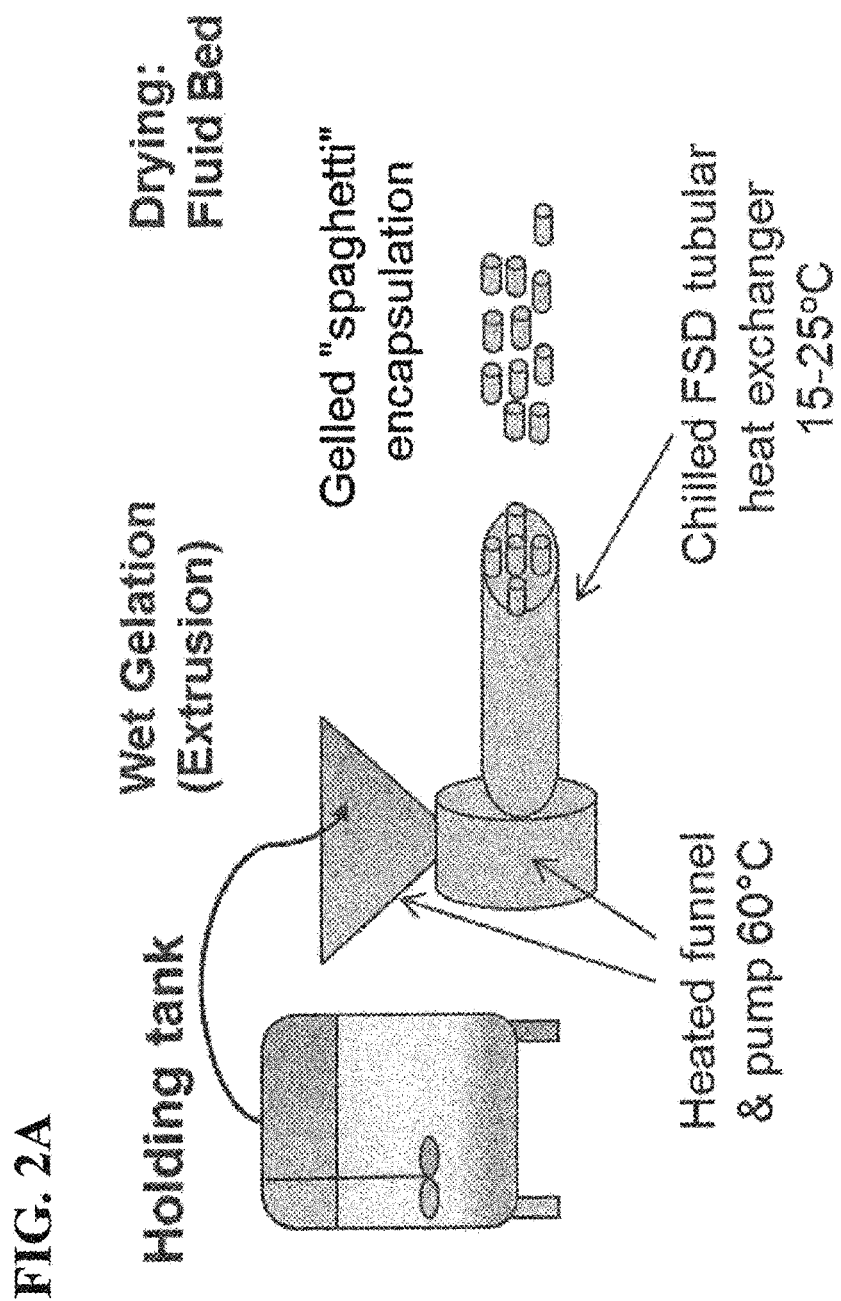
FIG. 2A is a schematic diagram of a system that can be used in an embodiment of a second method of making a food grade powder that reduces at least one symptom of human allergy to cats (the "extrusion method").
Figure 2B:
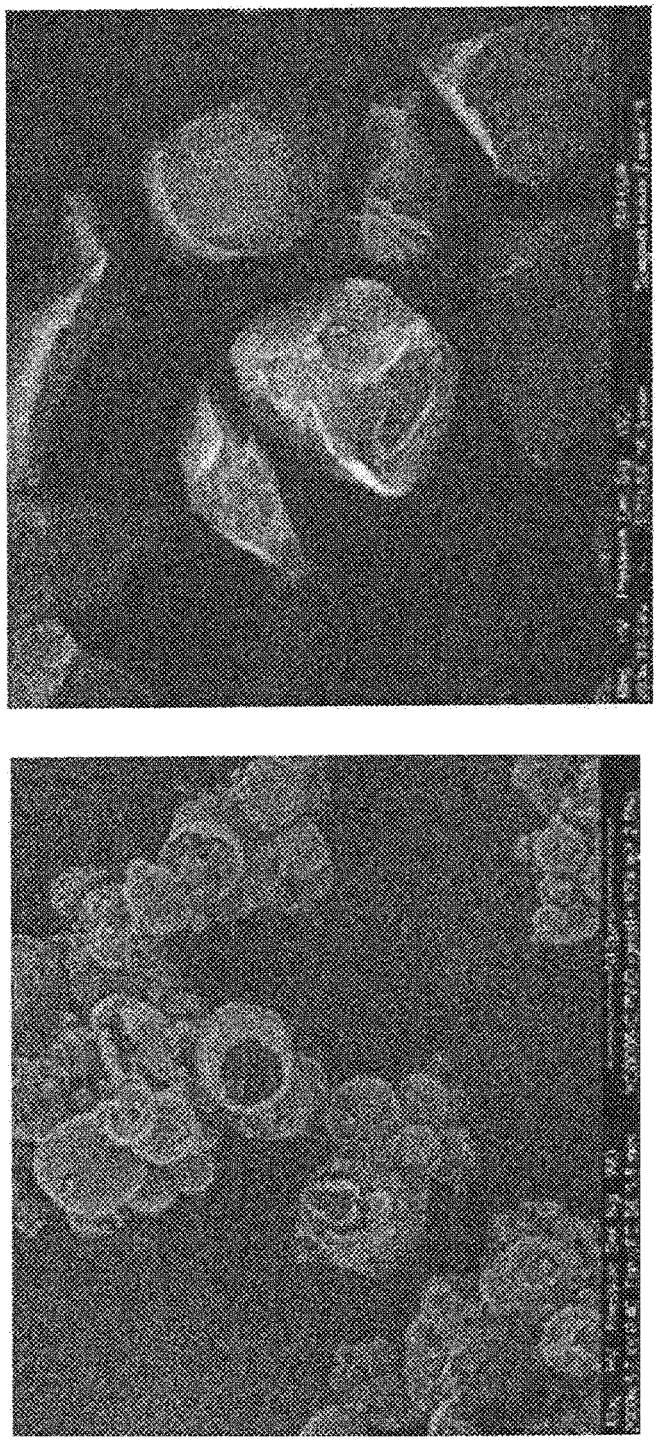
FIG. 2B contains comparative photographs between an embodiment of a food grade powder made by the extrusion method and a food grade powder made by conventional spray drying.
Figure 2C:
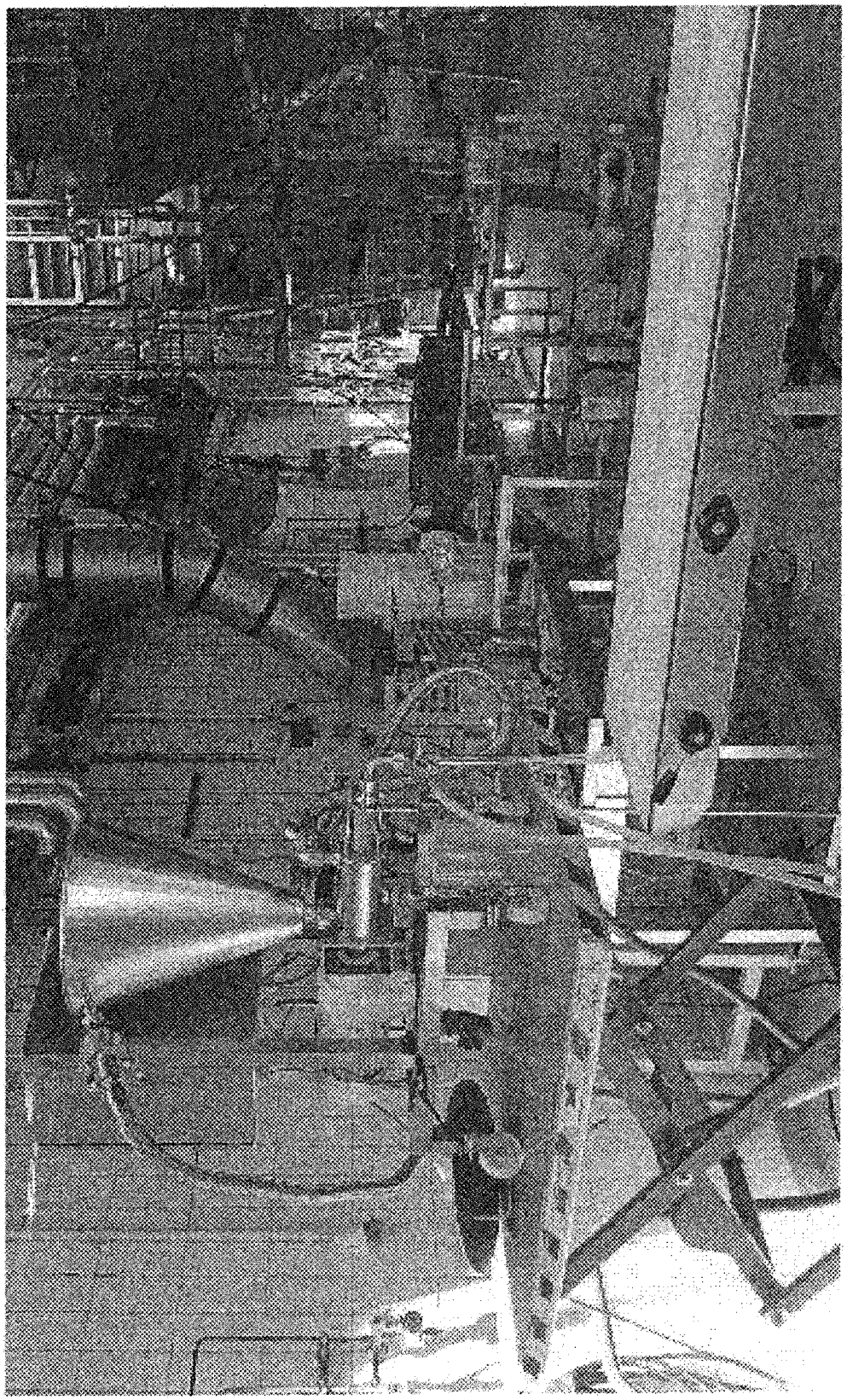
FIG. 2C is a photograph of an embodiment of a system that can be used in the extrusion method.
Figure 2D:
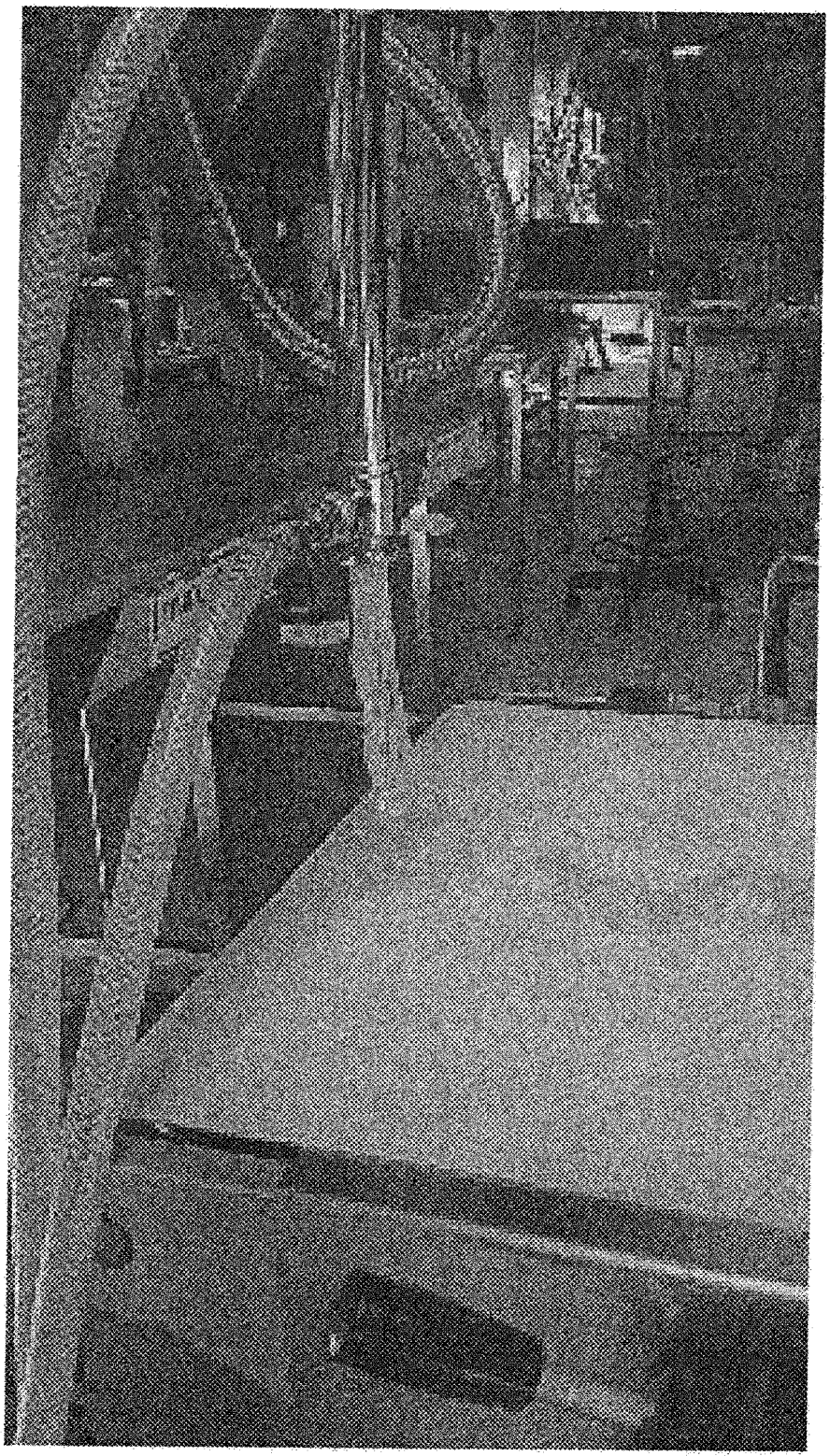
FIG. 2D is a photograph of the system of FIG. 2C in use.

FIG. 2A is a schematic diagram of a non-limiting example of a suitable apparatus for performing this method, FIG. 2B contains photographs comparing the dense powder structure achieved by this method to the highly porous powder structure obtained by conventional spray drying, and FIG. 2C is a photograph of a non-limiting example of a suitable apparatus for performing this method. The heat exchanger can extrude the hydrogel in a desired shape, for example strands of hydrogel as shown in the photograph of FIG. 2D.

In an embodiment, the extruded hydrogel is immersed in a composition comprising calcium chloride before the drying. In another embodiment, the extruded hydrogel is immersed in a composition comprising potassium chloride before the drying, for example a bath of about 1 mM potassium chloride. In one aspect, the extruded hydrogel can be dried in a drying tunnel or fluid bed drier. The method can comprise milling the dried hydrogel to a predetermined size to form the powder.

For example, the strands (or cut pieces thereof) of extruded material can be dried in a fluid bed drier with an inlet air temperature of 20-25° C. at an air flow of 120 m$^3$/minute for 30 to 60 minutes, then at about 40° C. at an air flow of about 120 m$^3$/minute for an additional 60 to 90 minutes. The resulting dry material can be collected and either used "as-is" or milled to further reduce the particle size to a desired size.

As another example, the strands (or cut pieces thereof) of extruded material can be dried in a drying tunnel with an inlet air temperature of 20-25° C. at an air flow of 20-80 m$^3$/minute for 30 to 60 minutes, then at about 40° C. at an air flow of 20-120 m$^3$/minute for an additional 60 to 90 minutes. The resulting dry material can be collected and either used "as-is" or milled to further reduce the particle size to a desired size.

As noted above, the present inventors surprisingly found that optimized spray drying conditions and also careful selection of gelatin properties (e.g., molecular weight) and wall materials could develop a formulation capable of being spray dried, with the resulting powder retaining its mucoadhesive properties. Therefore, yet another aspect of the present disclosure is a food grade powder that provides sustained release of an anti-Fel D1 molecule and comprises a spray-dried hydrogel comprising the anti-Fel D1 molecule and 0.5 to 90.0 wt. % of gelatin. The powder comprising the spray-dried hydrogel has a density of about 0.1 g/cm$^3$ to about 0.6 g/cm$^3$, about 0.265 g/cm$^3$ to about 0.5 g/cm$^3$, or in one aspect, about 0.4 g/cm$^3$ to about 0.5 g/cm$^3$. The anti-Fel D1 molecule can be encapsulated in the spray-dried hydrogel. In an embodiment, the gelatin can be the only biopolymer capable of gelling below 60° C. in the spray-dried hydrogel. In some aspects, the gelatin can have a bloom value of 40 to 300, or 40 to 200, or even about 100. In one aspect, the gelatin can be Type A gelatin (acid-treated).

In one embodiment, the powder can comprise 10.0 to 99.5 wt. % of a source of the anti-Fel D1 molecule (e.g., partially defatted egg yolk powder from an avian immunized with Fel D1). In one aspect, the powder can comprise 10.0 to 80.0 wt. % of the gelatin and 20 to 90 wt. % of the source of the anti-Fel D1 molecule. In another aspect, the powder can comprise 25.0 to 80.0 wt. % of the gelatin and 20 to 75 wt. % of the source of the anti-Fel D1 molecule. In still another aspect, the powder can comprise 25.0 to 60.0 wt. % of the gelatin and 40 to 75 wt. % of the source of the anti-Fel D1 molecule.

Figure 3:
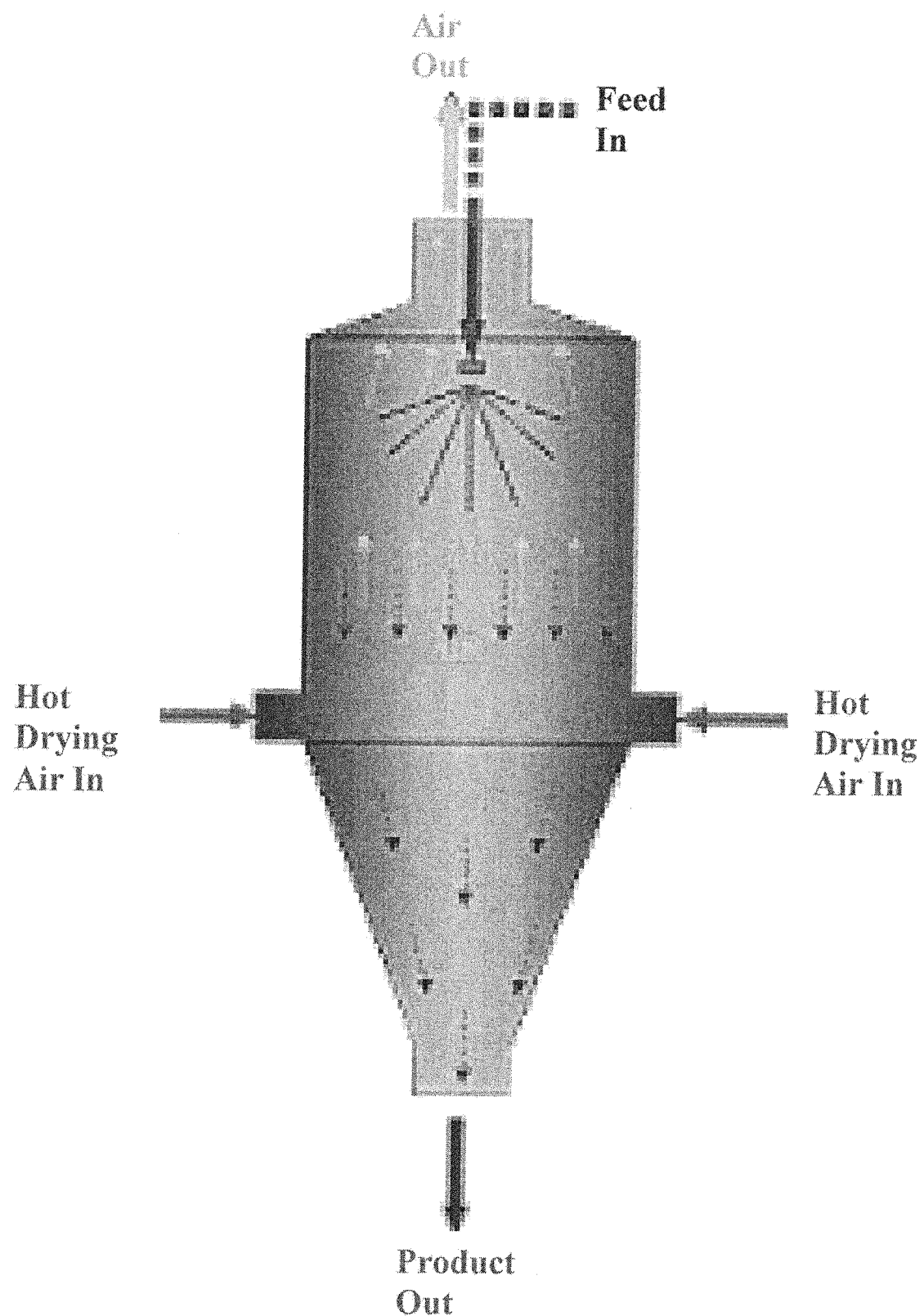
FIG. 3 is a schematic diagram of a system that can be used in an embodiment of a third method of making a food grade powder that reduces at least one symptom of human allergy to cats (the "controlled spray drying method").

FIG. 3 shows a non-limiting example of a suitable apparatus for making this embodiment of the powder. The method for making this embodiment of the powder can comprise spray drying a solution comprising an anti-Fel D1 molecule and 5.0 to 20.0 wt. % of gelatin having a bloom value of 40 to 200 to form a dried hydrogel in which the anti-Fel D1 molecule is encapsulated. In an embodiment, the gelatin can be the only biopolymer that is capable of gelling below 60° C. in the solution. In another embodiment, the gelatin can have a bloom value of 40 to 200, or in one aspect, about 100.

The solution can comprise 0.5 to 30.0 wt. % of a source of the anti-Fel D1 molecule (e.g., partially defatted egg yolk powder from an avian immunized with Fel D1). In one aspect, the solution can comprise 2.0 to 15.0 wt. % of the gelatin and 2.0 to 20.0 wt. % of the source of the anti-Fel D1 molecule; and in one specific aspect, 7.5 to 12.5 wt. % of the gelatin and 5 to 20 wt. % of the source of the anti-Fel D1 molecule.

Yet another aspect of the present disclosure is a method of reducing symptoms of human allergy to a cat. The method comprises orally administering to the cat an effective amount of any of the food grade powders disclosed herein and/or a food grade powder resulting from any of the methods disclosed herein. The powder can be administered as part of a pet food further comprising at least one component selected from the group consisting of protein, fat, carbohydrate, vitamin and mineral. The method can bind the anti-Fel D1 molecule to the Fel D1 in the cat's mouth and thereby prevent the Fel D1 from inducing an allergic reaction in a human susceptible to or suffering from an allergy caused by Fel D1.

EXAMPLES

By way of example and not limitation, the following non-limiting examples are illustrative of compositions and methods for reducing symptoms of human allergy to cats in embodiments provided by the present disclosure.

Example 1

A first study was performed to understand the impact of different drying approaches on the release of anti-Fel D1 IgY from hydrogels in order to help guide the development of manufacturing approaches for the delivery system. Two different hydrogel formulations; i) a simple gelatin-only formulation and ii) a gelatin/kappa-carrageenan co-gel formulation were created using two approaches; i) direct spray drying and ii) beadlet formation followed by drying. The central hypothesis was that gelation of the hydrogel before drying would result in a better capsule structure that is more able to slow the rate of anti-Fel D1 IgY release from the dried hydrogel.

This study found that the type of drying used to create hydrogel powders can have a major impact on the rate of anti-Fel D1 IgY release from hydrogel microcapsules. It was found that gelling the hydrogel formulation before drying resulted in microcapsules with thicker and denser wall structures. The resulting "gel→dried" microcapsules had an anti-Fel D1 IgY release rate 2.75 times slower than spray dried microcapsules. No difference in anti-Fel D1 IgY release rate was observed between simple gelatin-only microcapsules and complex gelatin/kappa-carrageenan co-gels. In wet hydrogels of gelatin/kappa-carrageenan co-gels, the release of anti-Fel D1 IgY from the co-gels was ten times slower than from gelatin-only gels.

Previous work within encapsulation assessed several different technologies (i.e., hydrogels, self-assembled structures, liposomes, and water-in-oil emulsions) to enhance the residence time of anti-Fel D1 IgY in cats' mouths. Overall, type A gelatin biopolymer hydrogels were found to be a leading technology because they had high encapsulation efficacy and inherent mucoadhesion.

Figure 4:
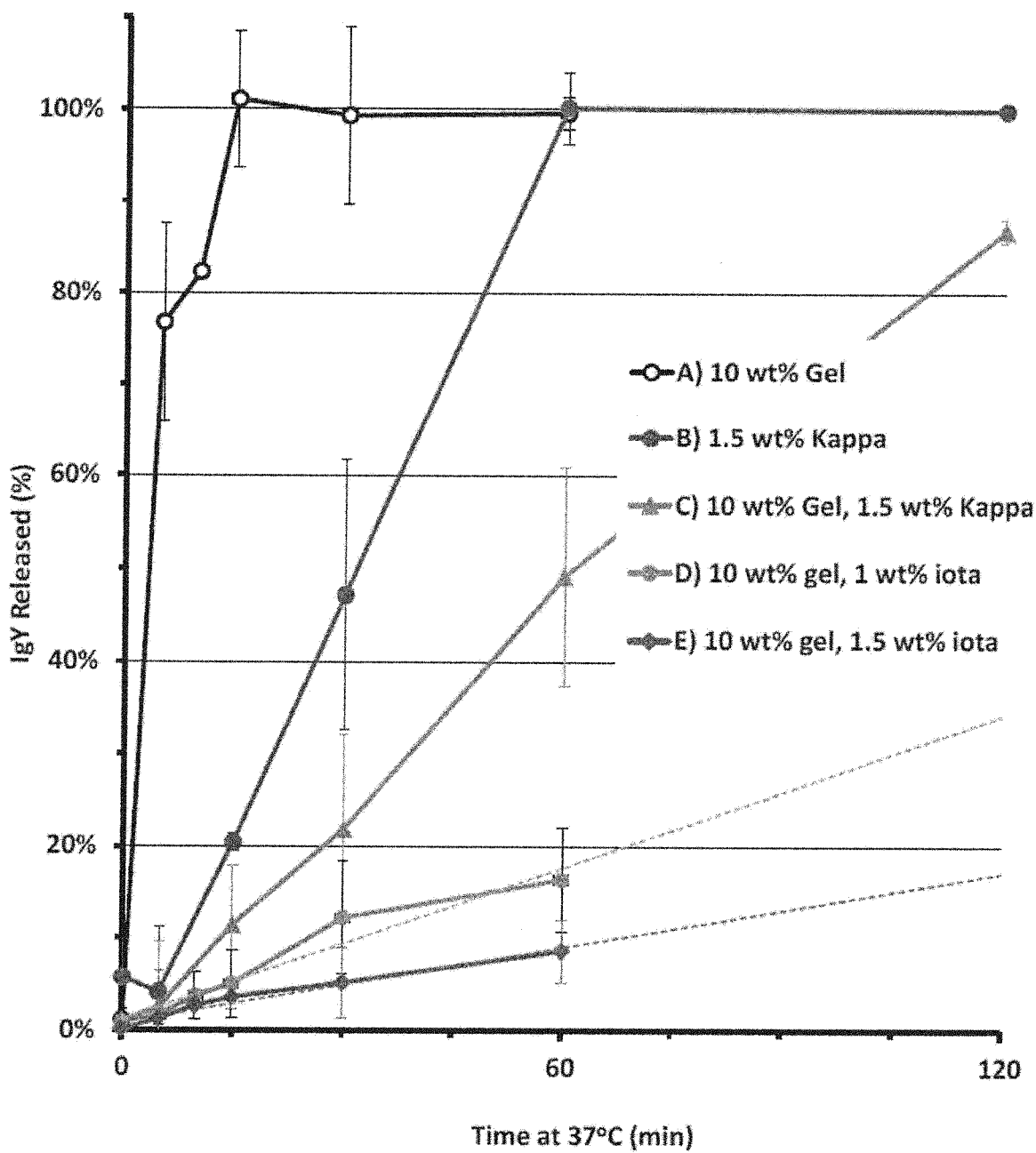
FIG. 4 is a graph of relative anti-Fel D1 IgY release over time from hydrogels of different compositions.

As shown in FIG. 4, a limitation of simple gelatin (10 wt. %) hydrogels is that they rapidly release all the encapsulated IgY when exposed to oral conditions (37° C. and simulated saliva). However, combining the gelatin hydrogel with a second hydrogel (e.g. agar, carrageenan) was found to enable the wet gelatin/kappa-carrageenan hydrogels to release anti-Fel D1 IgY over two hours. Surprisingly, all the co-gels had much slower anti-Fel D1 IgY release kinetics compared to simple hydrogels of gelatin alone or kappa-carrageenan alone, highlighting the unique synergy of combining the two biopolymers.

These hydrogels have high Aw (>0.6) which presents significant risks to the stability of anti-Fel D1 IgY from microbial spoilage, protein oxidation/denaturation and enzymatic degradation. Therefore these hydrogel structures must be dried without losing their ability to have a sustained release of anti-Fel D1 IgY over 2 to 4 hours. Hydrogel matrices can be dried using a number of approaches, each having an impact on the final powder structure and hence IgY release kinetics. The most conventional approach is spray drying, where the parent solution is directly dried in an atomized air stream without the solution passing through a gel state. A second approach is "gel→drying" where wet gel particles of the parent solution (e.g. by extrusion/dripping or prilling) are created before the drying step. The advantage of "gel→drying" approaches is that the structure of the hydrogel is more likely to be retained.

Figure 5A:
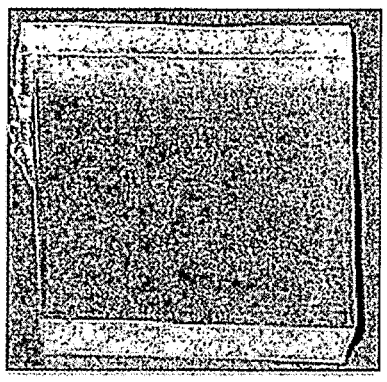
Figure 5B:
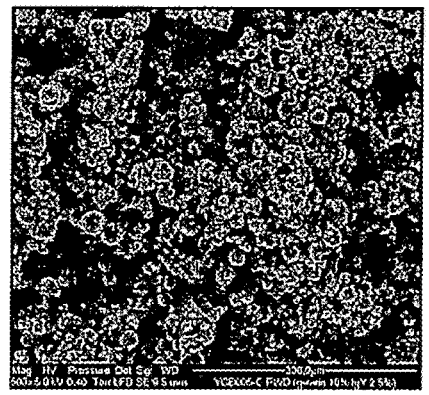
Figure 5C:
Figure 5D:
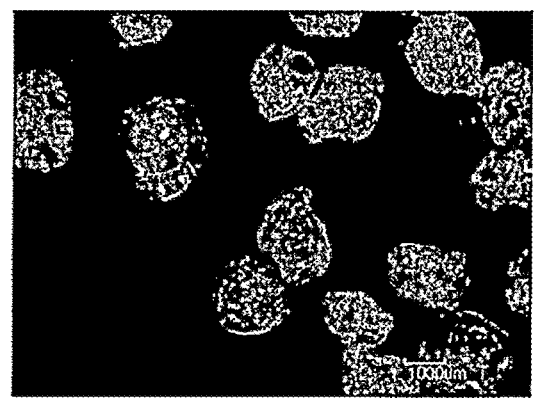

The effect of different drying techniques on anti-Fel D1 IgY release from hydrogels was first examined using simple hydrogels composed of gelatin. The parent solution consisted of 10 wt. % gelatin (type A bloom 280) and 2 wt. % egg yolk extract. As shown in FIGS. 5A-5D, different structures were obtained from this solution depending on whether the solution dried directly without gelling (FIG. 5B) or gelled before drying (FIG. 5D).

Figure 6B:
FIGS. 6A and 6B contain scanning electron microscopy (SEM) images of the cross section of powders made from solutions of 10 wt. % gelatin and 2 wt. % egg yolk extract. The powders were made.
Figure 6A:
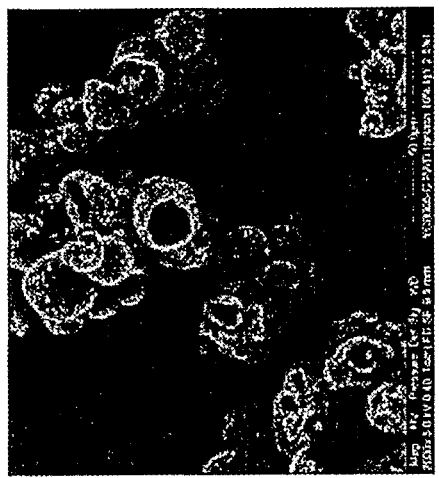

As shown in FIGS. 6A and 6B, when the solution was dried directly without gelling, the resulting power particles were small, very porous and even hollow (FIG. 6A). Such a powder structure is common for spray dried powders made from solutions of low total solids (12 wt. %). When the gelatin solution was gelled before drying, via dripping, the resulting powder particles were "shrunken" but had a thick, very dense powder wall structure (FIG. 6B).

Figure 7B:
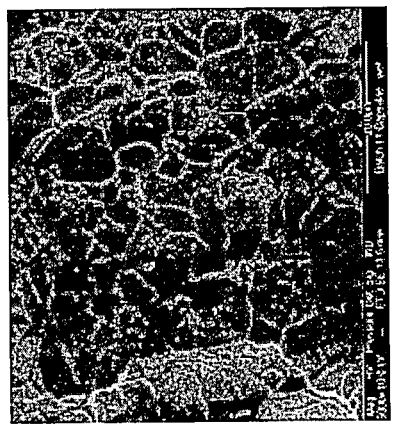
FIGS. 7A-D contain SEM analysis of the microstructural complexity of wet (A-C) and dry (D) beadlets. Composition: 9.81 wt. % gelatin (type A), 1.99 wt. % active ingredient, 1.47 wt. % WR78 carrageenan, and no salt.
Figure 7D:
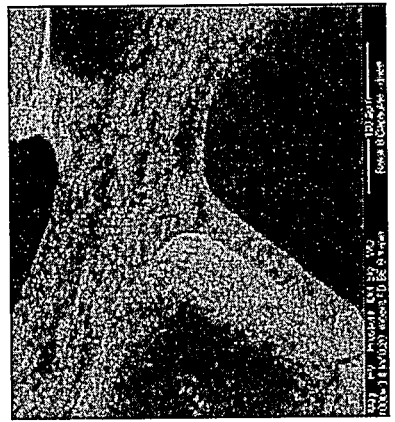
Figure 7A:
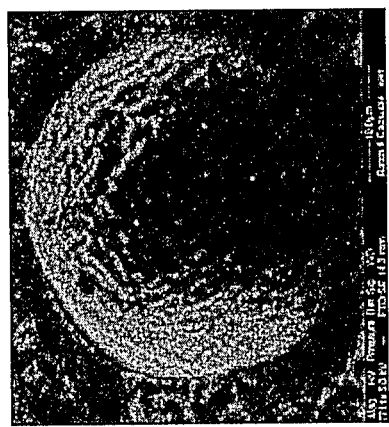
Figure 7C:
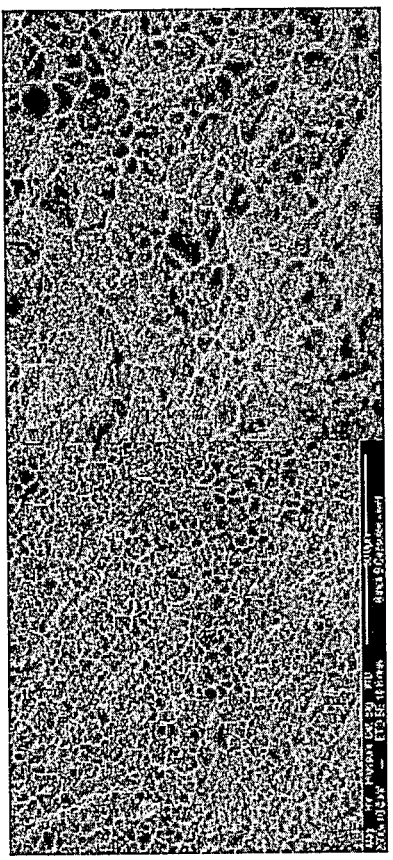
Figure 8:
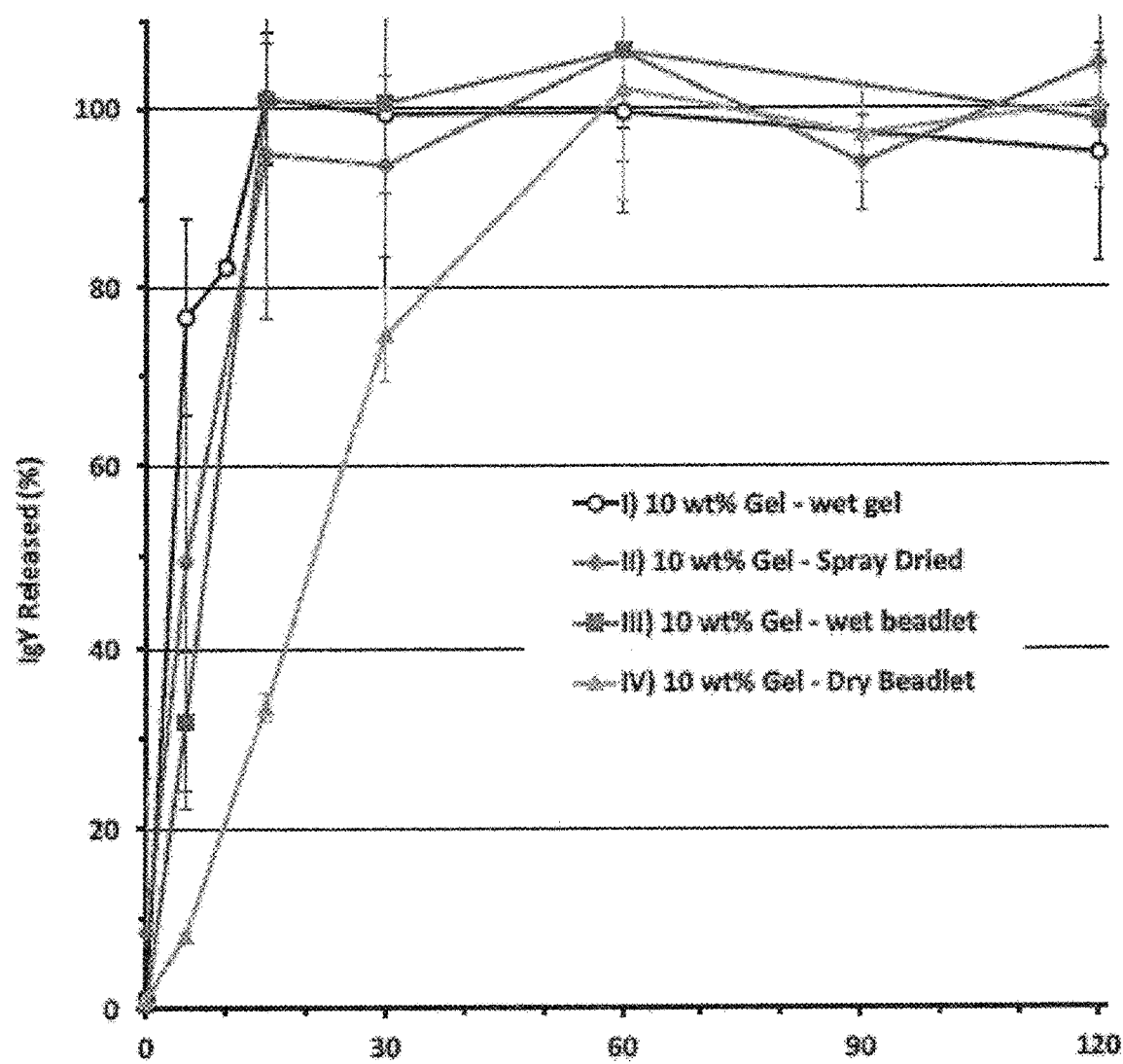
FIG. 8 is a graph of the impact of different gel preparation methods on anti-Fel IgY release from 10 wt. % gelatin type A hydrogels prepared with 2 wt. % egg yolk extract. Samples were prepared as: (I) gel piece 3×20×20 mm, (II) spray dried powder (Diameter, D4,3 32 μm), (III) wet beadlet produced by dripping into oil, and (IV) dried beadlet produced from (III).
Figure 9B:
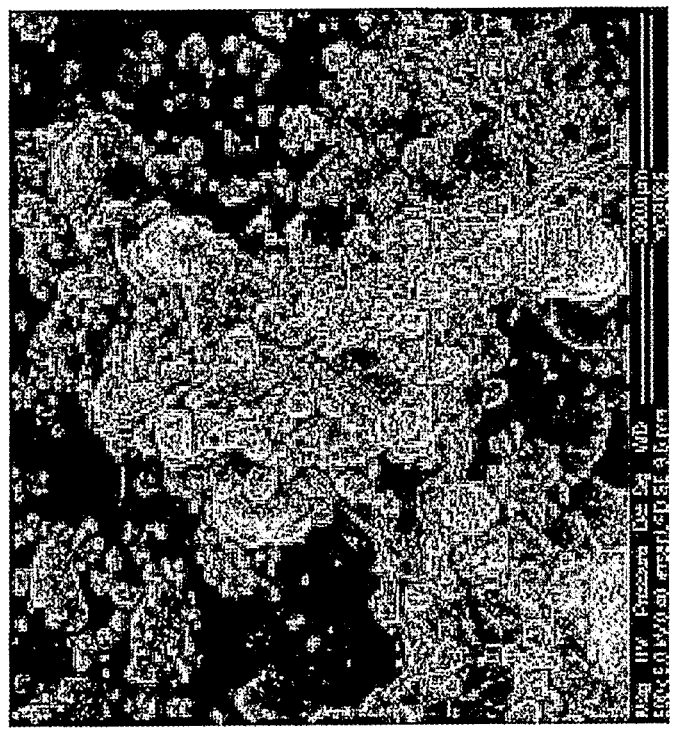
FIGS. 9A and 9B contain scanning electron micrographs of powders (A) and (B) produced by spray drying solutions of 10 wt. % gelatin, 1 wt. % kappa-carrageenan and 2 wt. % egg yolk extract.
Figure 9A:
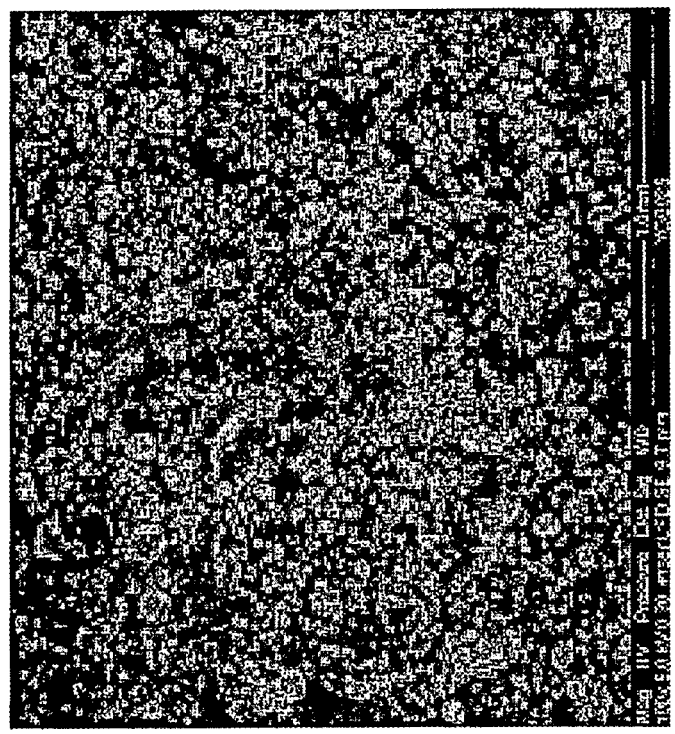
Figure 10C:
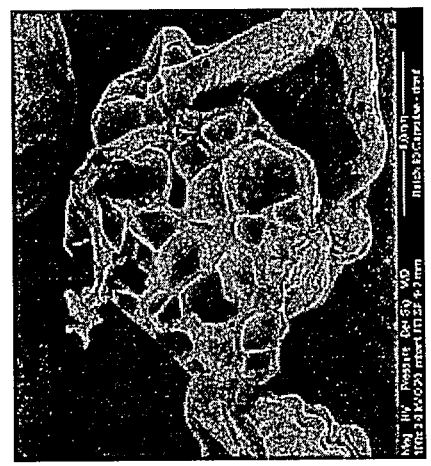
FIGS. 10A-10C contains photographs (A and B) and a scanning electron micrograph (C) of wet and dry beadlets produced by spray drying solutions of 10 wt. % gelatin (type A 280 bloom), 1 wt. % kappa-carrageenan and 2 wt. % egg yolk extract.
Figure 10B:
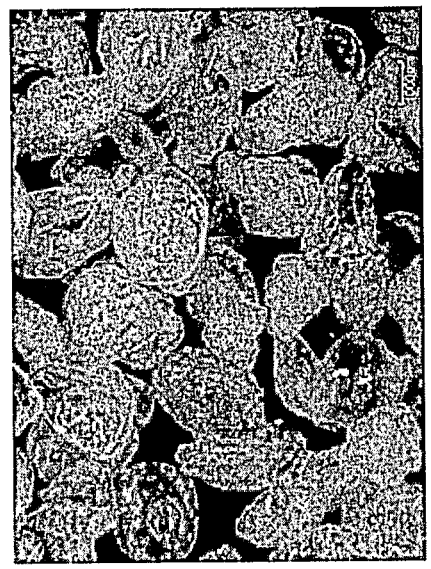
Figure 10A:
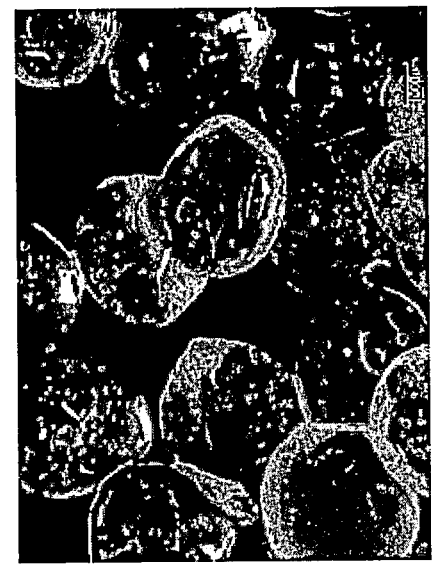
Figure 11A:
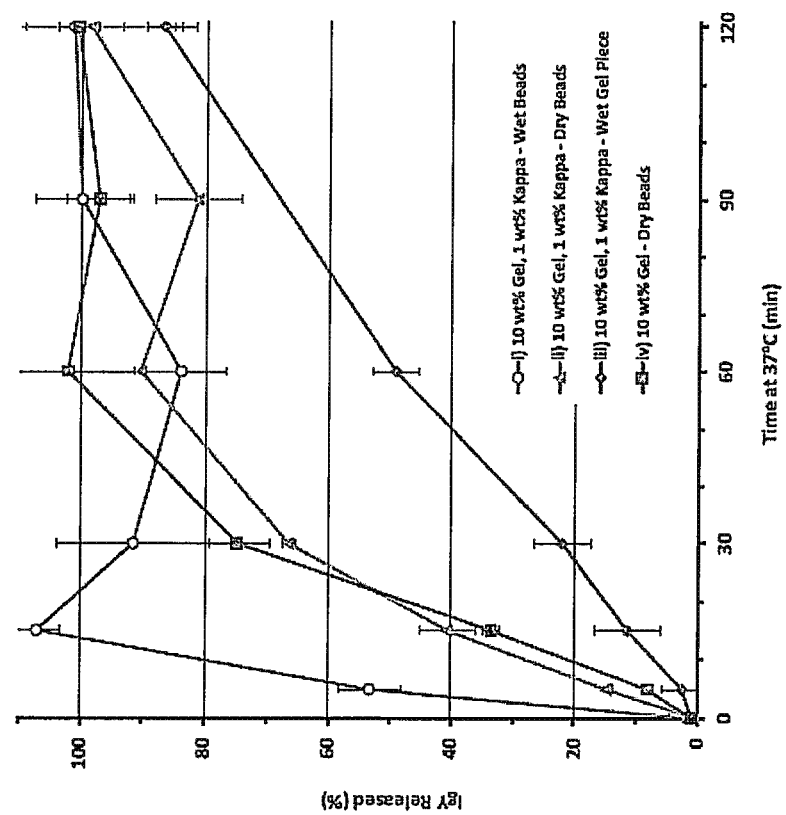
FIGS. 11A and 11B contain graphs showing the impact of different gel preparation methods on IgY release from 10 wt. % gelatin/1 wt. % kappa-carrageenan co-hydrogels prepared with 2 wt. % egg yolk extract. Samples were prepared as: (I) wet beadlets produced by dripping into 100 mM KCl solution, (II) dried beadlets produced from (I), (III) wet beadlets produced by dripping 10 wt. % gelatin (type A) and 2 wt. % egg yolk extract into oil, and (IV) dried beadlets produced from (III).
Figure 11B:
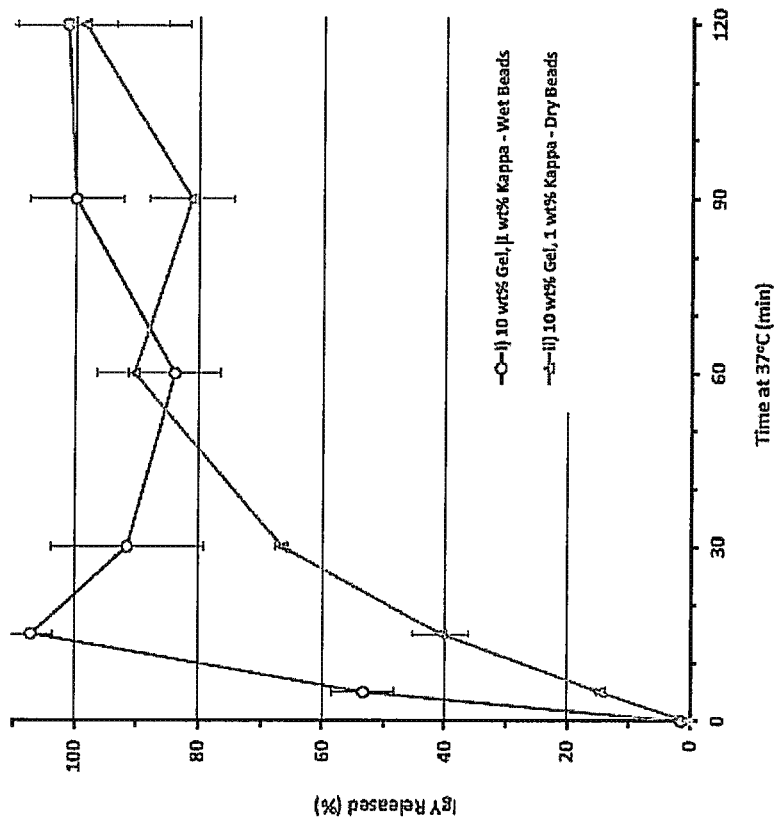

It was apparent that gelling the hydrogel before drying led to a markedly different structure than direct drying via spray drying. In order to gain insight into how this structure formed, the microstructure of the hydrogel was investigated using cryo-SEM with ice sublimation. FIG. 7A shows an outside view of a gel beadlet, and the only obvious element of its structure is that it is a sphere with a rough surface. A cross sectional analysis of the internal structure of the hydrogel can be achieved via freeze fracture SEM (FIGS. 7B and 7C). Both FIGS. 7B and 7C show that the gelatin hydro gel forms a mesh-like structure with a concentration of gelatin within the walls of each cell and large voids in the middle of each cell. Ice sublimation to remove the water in the structure shows the complexity of the cellular structure of the gelatin hydrogel, where there is a hierarchy of cellular structures that form a dense honeycomb matrix.

At initial viewing, one might think that the size of these cells (on the micrometer scale) is too large to limit the transport of IgY. However, examination of the fine structure of the wall of the gelatin gels reveals a very thick dense network (right panel of FIG. 7B). Upon drying, this cellular structure collapses upon itself to form the very dense walls of the powder particles.

Release of anti-Fel D1 IgY from these different particles was assessed by dispersing the powder in saline at 37° C. to mimic oral conditions. FIG. 8 presents the release of anti-Fel D1 IgY from different hydrogel structures: (I) wet gel pieces, (II) spray dried particles, (III) wet hydrogel beadlets and (IV) dry hydrogel beadlets.

The release of anti-Fel D1 IgY from the control sample, a gelled piece of the 10 wt. % gelatin, is shown in FIG. 8. Initially there was almost no anti-Fel D1 IgY when the gel piece was immersed in cold saline, showing that it had high IgY encapsulation efficiency (>98%). Upon immersion in saline at 37° C., there is a rapid increase in the amount of anti-Fel D1 IgY released, reaching 80% after 5 minutes and 100% after 15 minutes. Such rapid release is to be expected because 10 wt. % gelatin gels melt at temperatures above 25-30° C.

Likewise, the small wet gelatin beadlets rapidly released anti-Fel D1 IgY upon immersion in 37° C. saline, releasing 100% of the IgY over 15 minutes, again due to the melting of the hydro gel (FIG. 8). However, when the wet beadlets were dried, the release of anti-Fel D1 IgY slowed considerably: after 15 minutes, only 33.5% of IgY was released; at 30 minutes, 75% of IgY was released; and at 60 minutes, 100% of the IgY had been released (FIG. 8).

In contrast, directly drying gelatin solutions using spray drying did not lead to a retardation of IgY release. When spray dried gelatin powders were immersed in 37° C. saline, 50% of IgY was released after 5 minutes and 100% was released after 15 minutes (FIG. 8).

There is a striking difference in the rate of IgY release from spray dried powders compared to beadlets which were dried after gelling. This difference in IgY release is likely due to the difference in powder wall structure that is created by the two techniques. Spray drying led to capsules with a very thin wall structure, which would have a relatively high amount of surface area exposed to the saline. In contrast, drying gelatin solutions after gelation created powder particles which had a thick dense wall structure with a much lower relative amount of surface area exposed to the saline. It is likely that the lower surface area to volume ratios and the thicker/denser powder wall structure lead to much slower dissolution of the powder particles, resulting in much slower anti-Fel D1 IgY release.

The effect of different drying techniques on anti-Fel D1 IgY release from hydrogels was also examined using complex hydrogel co-gels composed of gelatin and carrageenan. The parent solution consisted of 10 wt. % gelatin (type A bloom 280), 1 wt. % kappa-carrageenan and 2 wt. % egg yolk extract. The effect of drying co-gel systems was assessed using (i) spray drying and (ii) dripping then fluidized bed drying.

FIG. 9A shows the appearance of a gelatin/kappa-carrageenan system after it has been spray dried. The spray dried gelatin/kappa-carrageenan powder consisted of hollow small particles with thin walls. In addition, aggregates were present in the structures which were found to be collections of small individual powder particles bound together by wires of the solution (FIG. 9B). Such a structure arises due to the high visco-elasticity of the parent 10 wt. % gelatin, 1 wt. % kappa-carrageenan solution. Highly visco-elastic solutions are difficult to atomize because the fluid bridge between two separating droplets retards complete droplet break-up resulting in the formation of strands. These strands can form fibers or aggregates by interacting with each other or the droplets in the spray tower. This was particularly the case when a rotating disc was used for atomization of the solution.

FIGS. 10A and 10B respectively show the appearance of wet gelatin/kappa-carrageenan co-beadlets and dry gelatin/kappa-carrageenan co-gel beadlets both produced by dripping the parent solution into 100 mM KCl. The process of gelling the beadlets then drying them creates powder particles that have a thick, very dense powder wall structure (FIG. 10C). Most powder particles had numerous air pockets within them, presumably a result of the loss of volume caused by the removal of the water. Sublimation experiments (not shown) similar to the gelatin-only system indicated that the co-gels had a similar wet beadlet structure compared to gelatin only systems.

FIG. 11A presents the release profiles of anti-FelD1 IgY from 10 wt. % gelatin/1 wt. % kappa-carrageenan co-gel spray dried powders. The gelatin/carrageenan co-gel spray dried powder releases 10% of IgY when it is placed in cold saline, indicating a high IgY encapsulation efficiency (~90%). However, when the co-gel powder was placed in 37° C. saline release of IgY was rapid, 30% of IgY was released after 5 minutes, 90% after 15 minutes and 100% after 30 minutes. This release rate is comparable to gelatin-only capsules and indicates that the presence of kappa-carrageenan does not have an impact on IgY release.

FIG. 11A also presents the release profiles of IgY from 10 wt. % gelatin/1 wt. % kappa-carrageenan co-gel beadlets in wet and dry format. Both the wet and dry beadlets exhibit high IgY encapsulation efficiency, releasing <2 wt % of IgY when the beadlets are dispersed in cold saline (4° C.). When the wet beadlets are immersed in 37° C. saline, IgY release is rapid: approximately 50% of IgY is released after 5 minutes, and 100% is released after 15 minutes. The dried co-gel beadlets exhibit slower IgY release compared to the wet co-gel beadlets. When the dried co-gel beadlets are placed in 37° C. saline, IgY release is slow: after 5 minutes 17% of IgY is released, rising to 40% after 15 minutes and 67% after 30 minutes, total IgY release occurs around 60 minutes.

Gelling the co-gel solution prior to drying results in a considerable slowing of IgY release rate (approx. 2.75 times). However, the IgY release rate of the dried co-gel beadlet is comparable to that of the dried gelatin beadlet (FIG. 11B). This indicates that the presence of kappa-carrageenan does not lead to an additional slowing in IgY release. This result is in contrast to earlier work with wet gels which demonstrated that gelatin/carrageenan co-gels had a 10 times slower IgY release rate compared to gelatin-only hydrogels (FIG. 11B). The lack of a slower IgY release rate for dried co-gels compared to dried gelatin gel beadlets (both in the dry and wet states) indicates that the carrageenan gel did not form properly. These beadlets were formed by dripping the co-gel solution into a 100 mM KCl solution because the viscosity of the solution was too high to drip. The original co-gel pieces were created by having the KCl in the co-gel solution prior to gelation. It is apparent from the previous experiments that removal of KCl from the co-gel solution could be a key reason why IgY release was not slowed down by the presence of the carrageenan in the co-gel.

In summary, the type of drying used to create hydrogel powders can have a major impact on the rate of IgY release from hydrogel microcapsules. Gelling the hydrogel formulation before drying was found to result in microcapsules with thicker and denser wall structures. The resulting "gel→dried" microcapsules had an IgY release rate 2.75 times slower than spray dried microcapsules. No difference in IgY release rate was observed between simple gelatin only microcapsules and complex gelatin/K-carrageenan co-gels. In wet hydrogels, gelatin/kappa-carrageenan co-gels provided release of IgY that was 10 times slower than from gelatin only gels.

Example 2

A second experiment was performed to investigate the dripping method disclosed herein that employs a gelation bath and the extrusion method disclosed herein that does not employ a gelation bath. An anti-Fel D1 IgY was utilized in a gelatin-carrageenan co-polymer gel.

Figure 12:
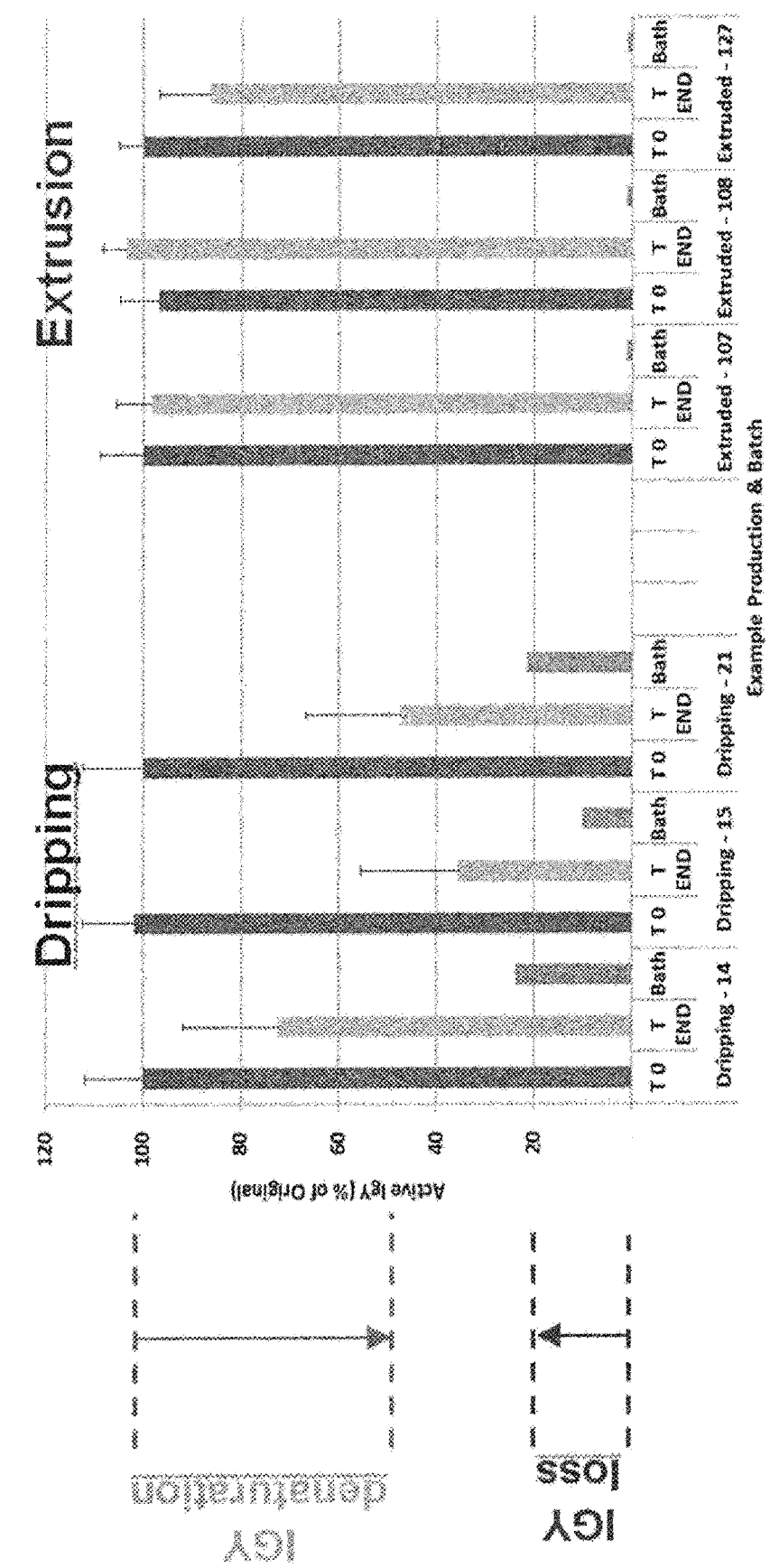
FIG. 12 contains graphs of experimental data regarding denaturation and encapsulation efficiency of anti-Fel D1 IgY encapsulated by the dripping and extrusion methods.

An oral delivery vehicle should have high content of the active molecule. Typical losses of the active molecule occur due to low encapsulation efficacy and denaturation of the IgY during processing/manufacture. The results of the dripping method and the extrusion method with respect to denaturation and encapsulation efficiency are shown in FIG. 12. Regarding denaturation of the anti-Fel D1 IgY, 20 to 60% of the IgY was lost during the manufacturing in the dripping method, and 0 to 15% of the IgY was lost during the manufacturing in the extrusion method. Regarding encapsulation of the anti-Fel D1 IgY, about 20% of the IgY was lost in the bath during the gelation step of the dripping method, and less than 1% of the IgY was lost during the extrusion method.

Figure 13B:
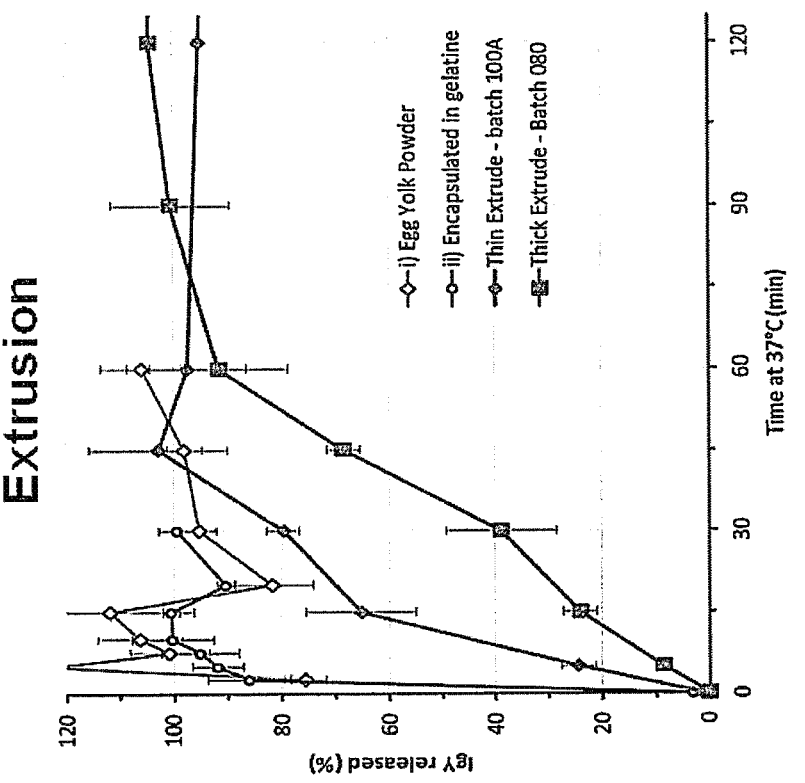
FIGS. 13A and 13B contain graphs of experimental data regarding controlled release of anti-Fel D1 IgY encapsulated by the dripping and extrusion methods.
Figure 13A:
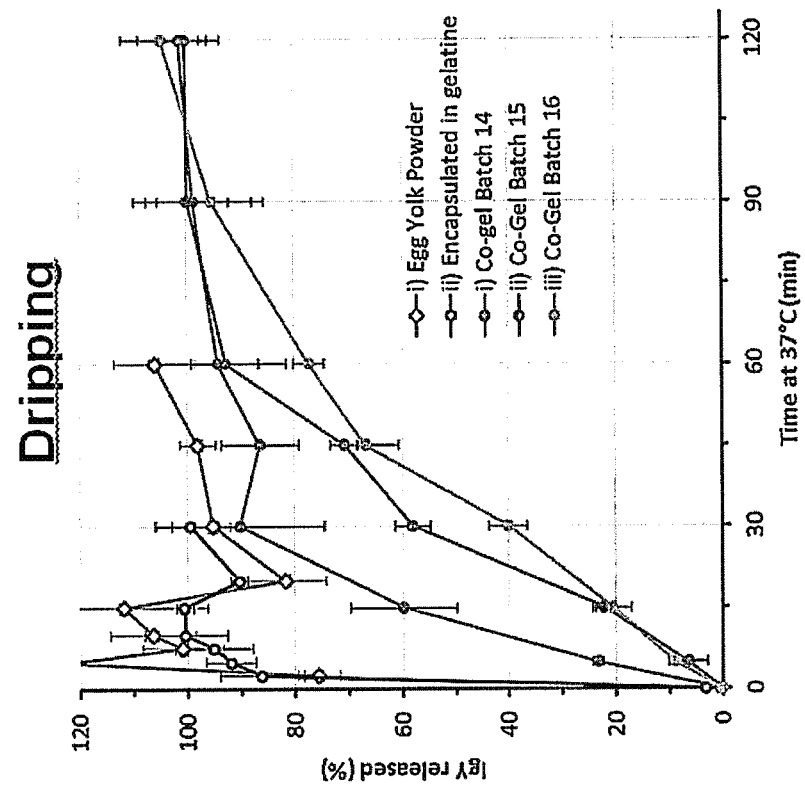

An oral delivery vehicle should also have controlled release of the active molecule; release of the anti-Fel D1 IgY in the cat's mouth occurs via dissolution. Accordingly, release of the anti-Fel D1 IgY was investigated in simulated saliva at 37° C. As shown in FIGS. 13A and 13B, the anti-Fel D1 IgY in egg powder had a fast release: 100% released in less than 5 minutes (control 1), and the anti-Fel D1 IgY encapsulated in gelatin alone also had a fast release: 90% in less than 5 minutes (control 2). The gelatin-carrageenan co-polymer gel allowed the time of 100% release to be tuned from 30 to 90 minutes when the dripping method was used and allowed the time of 100% release to be tuned from 30 to 60 minutes when the extrusion method was used.

Figure 14:
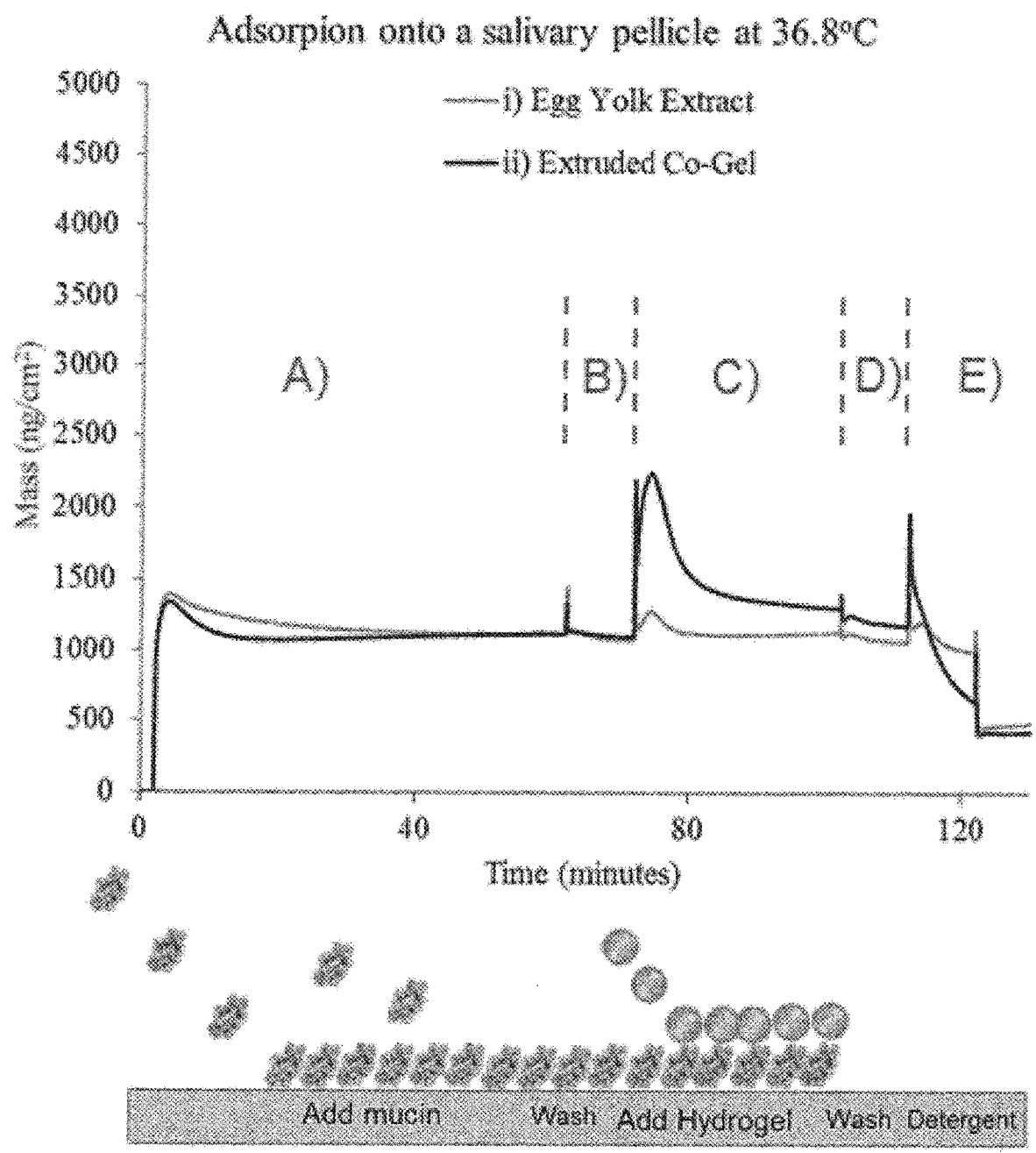
FIG. 14 is a graph of experimental data regarding oral adhesion of anti-Fel D1 IgY encapsulated by the extrusion method.

An oral delivery vehicle should also have oral adhesion because sustained release of the anti-Fel D1 IgY in the cat's mouth requires that the IgY stays in the mouth for some time. Mucoadhesive particles are thus advantageous because they can adhere to the salivary film. The oral adhesion of the particles from the extrusion method were compared to free IgY by investigating the interaction with human salivary film at about 37° C., specifically by measuring adsorption onto a salivary pellicle at 36.8° C. The results are shown in FIG. 14. Free IgY had no interaction with salivary film, but the particles from co-gel extrusion had a moderate increase in the interaction with the salivary film, clear deposition of particles on film (Δ mass period D).

Example 3

Figure 15:
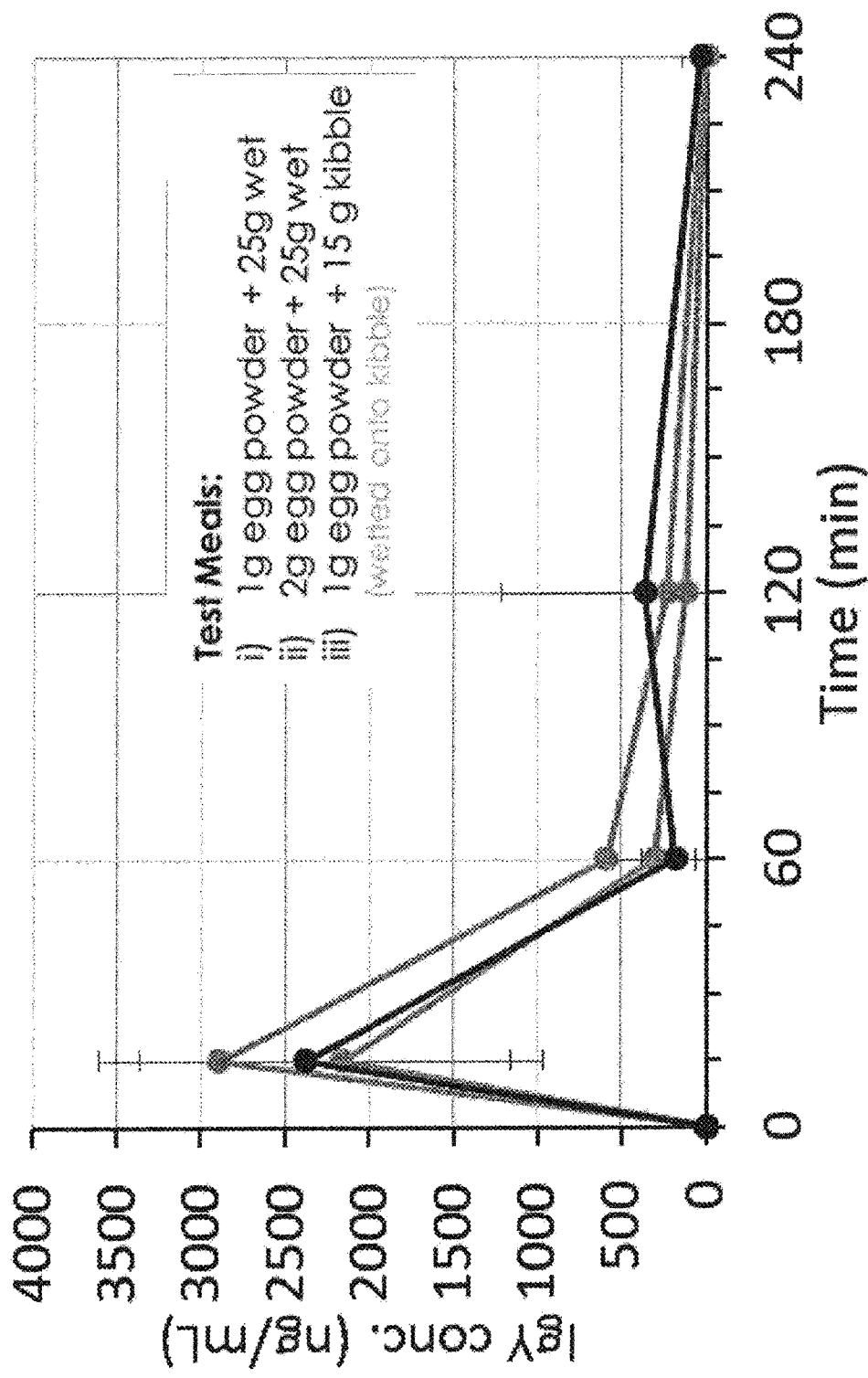
FIG. 15 is a graph of experimental data regarding oral residence time in vivo of unencapsulated anti-Fel D1 IgY.

To further investigate using encapsulation to improve the oral residence time of an anti-Fel D1 IgY, a third experiment was performed. FIG. 15 is a graph showing the concentration of the anti-Fel D1 IgY in cats' saliva after they were fed 1 g or 2 g of egg yolk containing anti-Fel D1 IgY with wet or dry food. Less than 5% of the anti-Fel D1 IgY was detected in the cat's mouth, the remainder was quickly swallowed.

Figure 16:
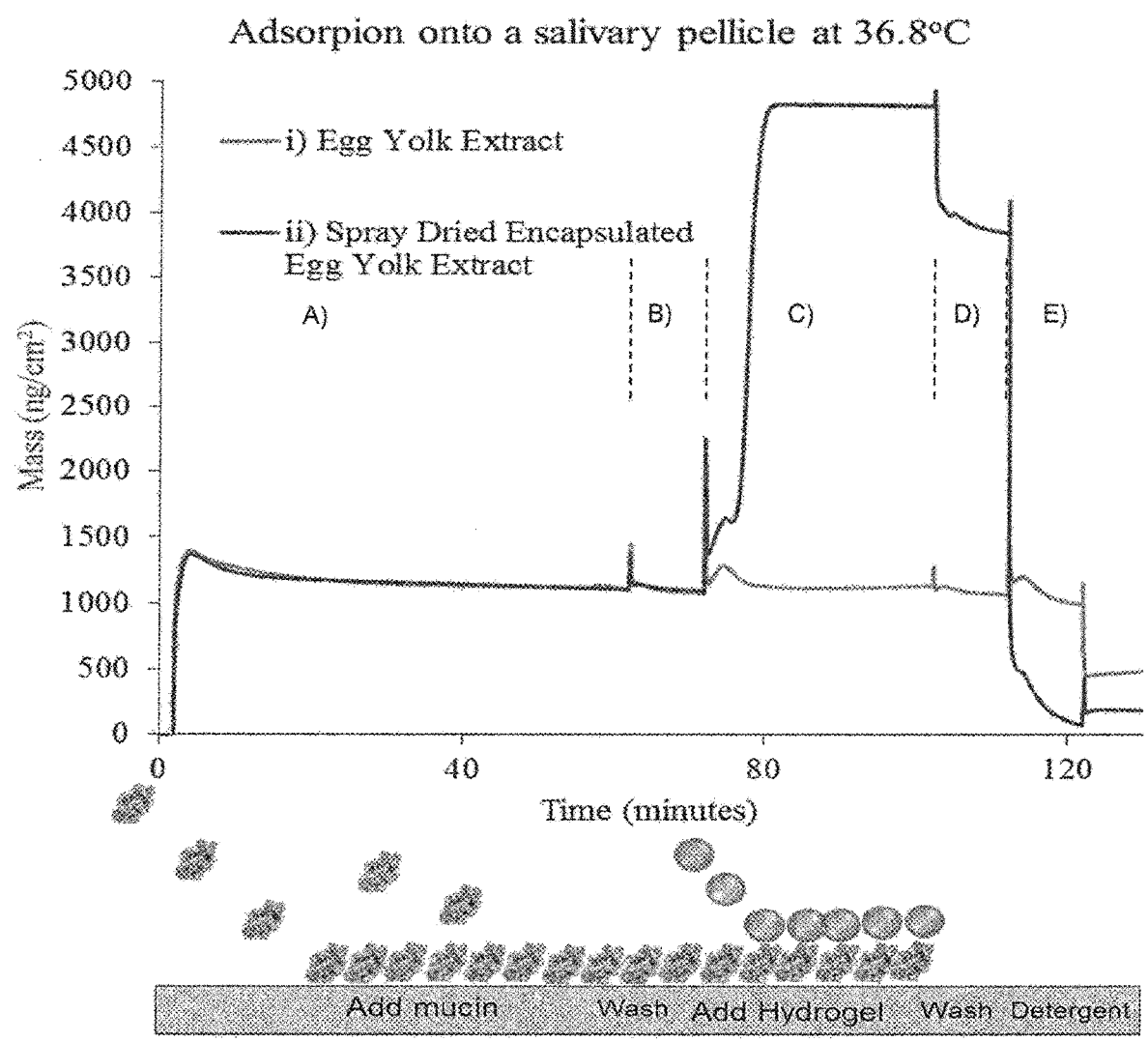
FIG. 16 is a graph of experimental data regarding oral adhesion of anti-Fel D1 IgY encapsulated by the controlled spray drying method.

The oral adhesion of the particles from the controlled spray-drying method were compared to free IgY by investigating the interaction with human salivary film at about 37° C., specifically by measuring adsorption onto a salivary pellicle at 36.8° C. The results are shown in FIG. 16. Free IgY had no interaction with salivary film, but the particles from the controlled spray-drying method had a considerable increase in the interaction with the salivary film, clear deposition of particles on film (Δ mass period D).

Example 4

A fourth experiment was performed in which the spray-dried gelatin/IgY mixture was further analyzed. Without being bound by theory, the present inventors believe that the mucoadhesion of the spray-dried gelatin/IgY mixture relies on a porous powder structure that allows some initial hydration, which creates mucoadhesion interactions through a combination of i) electrostatic interactions (positive charge on gelatin) and hydration/competition for water (i.e., the particles are sticky). The glassy co-gel of gelatin-carrageenan, while still effective, may have lower oral adhesion due to much slower hydration.

If a particle can be made to stick to the oral surface, oral residence time can be further enhanced by controlling the speed of dissolution. The powders of the dripping and extrusion methods disclosed herein control dissolution by powder porosity and controlled dis-assembly of carrageenan gels. The spray-dried gelatin/IgY mixture uses porous gelatin powders which have relatively quick in vitro dissolution, the main focus is maximizing oral adhesion. However, informal feedback from clinical trials suggests that in vivo dissolution is slower than observed in vitro and may be beneficial.

It is well known that creation of a powder from gelatin can be difficult. The main technical challenge is that the viscoelastic properties of gelatin solutions limit droplet break-up during atomization in the drier. If the solution has too high viscosity, or if the atomization is too rapid the solution creates filament structures rather than powder particles. This results in a "fluffy" powder which has a low density. A low powder density creates problems during powder handling, powder stability or when trying to apply it to a product as a coating.

As shown in FIG. 17, to overcome the problems of fluffy gelatin powders with low density, the present inventors found three factors that can improve density: (1) gelatin concentration—gelatin concentrations above 16% create highly filamentous powders and hence cannot be spray dried (Table 1—TJW 040 series—comparison ii); (2) gelatin molecular weight (bloom strength)—switching to a lower molecular weight gelatin (bloom 100 rather than 280) decreases filament formation increasing powder density (Table 1—comparison i); and (3) combining with other proteins/molecules—increasing the amount of active ingredient/excipient decreases filament formation increasing powder density (Table 1—TJW 040 series comparison ii).

Using these strategies the powder density could be increase from an unusable powder of 0.1-0.15 g/cm$^3$ for the TJW 020A sample to TJW 050 A and 106 powders whose density (0.265-0.3 g/$cm^3$) approaches that of commercial whey protein isolate (WPI) dairy powder (0.43 g/$cm^3$).

Example 5

Figure 18:
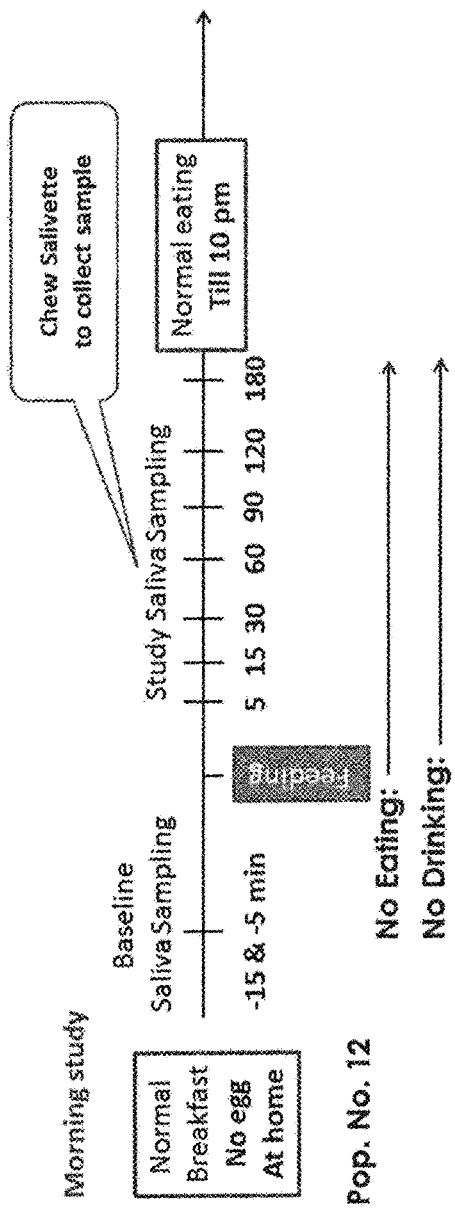
FIG. 18 is a schematic showing the design of the clinical trial used to assess the impact of encapsulation on IgY oral retention.
Figure 20:
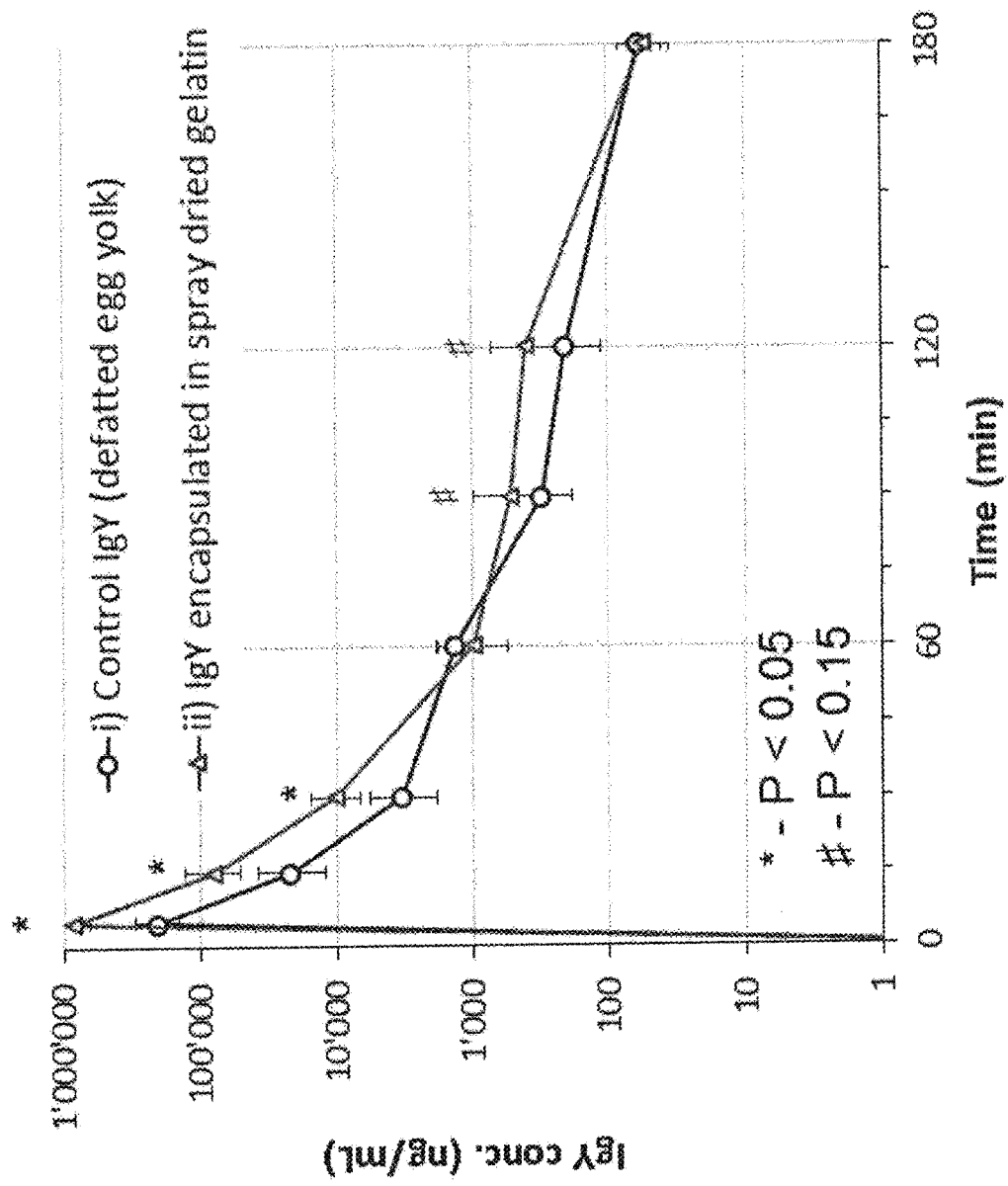
FIG. 20 is a graph showing the change in human saliva IgY concentration verses time across the two treatments i) 140 mg IgY delivered in 1 g egg powder, ii) 140 mg of IgY delivered as a spray dried powder of gelatin (type A, 100 bloom) and defatted egg yolk proteins. Error bars represent 95% confidence intervals n=12 participants.

A fifth experiment was performed that assessed the impact of encapsulation on the oral retention of IgY. Twelve human subjects were given two powders [i) IgY control—defatted egg yolk powder and ii) defatted egg yolk powder encapsulated in gelatin (type a, 100 bloom)] using a randomized cross over study design (FIG. 18), and asked to chew the powder for 30 seconds and then swallow. The composition and dose of the two test samples are given FIG. 19. Oral retention of IgY was assessed by measuring IgY concentration in saliva at baseline and at various time points as per clinical trial scheme outlined in FIG. 18. Measures of oral retention were; maximum concentration ($C_{max}$) and area under the curve (AUC).

FIG. 20 (Sample i) presents the average change in IgY concentration (ng·$ml^{-1}$) in participants saliva over time for the control IgY and IgY encapsulated in spray dried gelatin. After consumption of the control IgY, IgY concentration peaked at 206645±71911 ng·$ml^{-1}$ at 5 minutes (first time point). Salary IgY concentration then underwent an exponential decrease to 21502±6095 ng·$ml^{-1}$ at 15 minutes, 3224±905 ng·$ml^{-1}$ at 30 minutes, 1329±480 ng·$ml^{-1}$ at 60 minutes, plateauing at 200 to 300 μg·mL-1 two hours after consumption of the control IgY (defatted egg yolk powder). The average total amount of IgY detected in the human mouth was between 1.95 mg (single integration) and 3 to 3.5 mg (double exponential pk integration). The average amount of IgY detected in the human subjects mouth was between 1.6 and 2.8% of the original amount administered (~123 mg).

FIG. 20 (Sample ii) also presents the effect of encapsulation on human salivary IgY concentration. The spray dried encapsulated IgY had a $C_{max}$ of 871,000 ng·$mL^{-1}$ at 5 minutes which was 4.2 times larger than the control IgY (p<0.001). Salivary IgY concentration then underwent an exponential decrease to 81,500 ng·$mL^{-1}$ at 15 minutes, 10,200 ng·$mL^{-1}$ at 30 minutes, 980 ng·$mL^{-1}$ at 60 minutes plateauing at 400 to 500 ng·$mL^{-1}$ two hours after consumption of the control IgY (defatted egg yolk powder). The salivary concentration of IgY after consumption of the spray dried encapsulated IgY was 4 times larger than the control IgY for the first 30 minutes (p<0.05). Whilst salivary IgY concentration of the spray dried encapsulated IgY and the control IgY were the same 60 minutes after ingestion, the spray dried encapsulated salivary IgY concentration was double the control at 90 and 120 minutes (p<0.15). The total amount of IgY detected for the spray dried encapsulated IgY was 7.8 (trapezoid integration) to 13.2 (double exponential pk integration) mg of IgY, which equates to 6.4 to 10.7% of the administered dose. These results highlight that encapsulation of IgY in mucoadhesive gelatin using spray drying increases the efficacy (both $C_m$ax and AUC) of IgY by a factor of 4 (p<0.001).

It should be understood that various changes and modifications to the presently embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A food grade powder providing sustained release of an anti-Fel D1 molecule, the food grade powder comprising a dried hydrogel and the anti-Fel D1 molecule; wherein the dried hydrogel is a co-gel comprising carrageenan and a member selected from the group consisting of gelatin, collagen peptides, and gelatin and collagen peptides; wherein the anti-Fel D1 molecule is encapsulated in the dried hydrogel.

2. The food grade powder of claim 1, wherein the gelatin or the gelatin and collagen peptides are from Type A porcine gelatin having a positive charge at a pH below 7.0.

3. The food grade powder of claim 1, wherein the carrageenan is selected from the group consisting of (i) kappa-carrageenan, (ii) iota-carrageenan, (iii) a physical mixture of kappa-carrageenan and iota-carrageenan and (iv) a co-polymer of kappa-carrageenan and iota-carrageenan.

4. The food grade powder of claim 1, wherein the gelatin and the carrageenan are the only biopolymers in the dried hydrogel.

5. The food grade powder of claim 1, wherein the dried hydrogel is a spray-dried hydrogel comprising the anti-Fel D1 molecule and 0.5 to 90 wt. % of gelatin, and the powder has a density of about 0.265 to about 0.3 g/$cm^3$.

6. The food grade powder of claim 5, wherein the gelatin and collagen peptides have a molecular weight between 2,000 and 1 million Daltons and a bloom value of 40 to 300.

7. The food grade powder of claim 5, comprising 25.0 to 60.0 wt. % of the gelatin and 40 to 75 wt. % of a source of the anti-Fel D1 molecule.

8. A method of reducing symptoms of human allergy to a cat, the method comprising orally administering to the cat an effective amount of the food grade powder of claim 1.

9. The method of claim 8, wherein the composition is administered as part of a pet food further comprising at least one component selected from the group consisting of protein, fat, carbohydrate, vitamin and mineral.

* * * * *